United States Patent
Chen et al.

(10) Patent No.: US 6,695,827 B2
(45) Date of Patent: Feb. 24, 2004

(54) ABSORBENT ARTICLE HAVING GOOD BODY FIT UNDER DYNAMIC CONDITIONS

(75) Inventors: Fung-jou Chen, Appleton, WI (US); Julie M. Bednarz, Neenah, WI (US); Jeffrey D. Lindsay, Appleton, WI (US); Joseph DiPalma, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 10/306,568

(22) Filed: Nov. 27, 2002

(65) Prior Publication Data

US 2003/0083631 A1 May 1, 2003

Related U.S. Application Data

(63) Continuation of application No. 09/165,871, filed on Oct. 2, 1998, now Pat. No. 6,503,233.

(51) Int. Cl.⁷ .................................................. A61F 13/15
(52) U.S. Cl. ................................................... 604/385.01
(58) Field of Search ................................ 604/378, 379, 604/380, 385.01

(56) References Cited

U.S. PATENT DOCUMENTS

| | | |
|---|---|---|
| 1,843,037 A | 1/1932 | Mathey |
| 2,064,431 A | 12/1936 | Jurgensen ................. 128/290 |
| 2,331,355 A | 10/1943 | Strongson |
| 2,747,575 A | 5/1956 | Mercer |
| 2,787,271 A | 4/1957 | Clark ........................ 128/290 |
| 2,952,260 A | 9/1960 | Burgeni ..................... 128/290 |
| 3,029,817 A | 4/1962 | Harwood et al. ........... 128/290 |
| 3,036,573 A | 5/1962 | Voigtman et al. .......... 128/290 |
| 3,143,113 A | 8/1964 | Mills ......................... 128/290 |
| 3,211,147 A | 10/1965 | Pherson et al. ............. 128/284 |
| 3,230,955 A | 1/1966 | Joa et al. .................... 128/290 |
| 3,343,543 A | 9/1967 | Glassman ................... 128/290 |
| 3,395,201 A | 7/1968 | Kalwaites .................... 264/45 |
| 3,395,708 A | 8/1968 | Hervey et al. |
| 3,411,504 A | 11/1968 | Glassman ................... 128/290 |
| 3,430,630 A | 3/1969 | Megison et al. ............ 128/290 |

(List continued on next page.)

FOREIGN PATENT DOCUMENTS

| | | |
|---|---|---|
| AU | 650912 | 4/1992 |
| CA | 803531 | 1/1969 |
| CA | 884608 | 11/1971 |

(List continued on next page.)

OTHER PUBLICATIONS

US 5,674,210, 10/1997, Coles et al. (withdrawn)
McCauley, N.; *Vibrating and Gyrating Screeners: Proper Installation Yields Top Performance, Powder and Bulk Engineering*, vol. 13, No. 12, Dec. 1999, pp. 35–39.

(List continued on next page.)

*Primary Examiner*—Weilun Lo
*Assistant Examiner*—Michael Bogart
(74) *Attorney, Agent, or Firm*—Pauley Petersen & Erickson

(57) ABSTRACT

An absorbent article with improved body fit wherein a combination of downward-deflecting crease lines and an upward-deflecting shaping line are used in outer and central absorbent members, respectively, to achieve a form-fitting geometry in the crotch region while also enhancing control over fluid flow in the article. Embodiments with wicking barriers between the outer and central absorbent members are especially useful in achieving leakage reduction.

36 Claims, 9 Drawing Sheets

U.S. PATENT DOCUMENTS

| | | |
|---|---|---|
| 3,468,311 A | 9/1969 | Gallgher .................... 128/296 |
| 3,554,862 A | 1/1971 | Hervey et al. |
| 3,556,932 A | 1/1971 | Coscia et al. ............... 162/166 |
| 3,556,933 A | 1/1971 | Williams et al. ............ 162/167 |
| 3,559,650 A | 2/1971 | Larson ...................... 128/290 |
| 3,575,174 A | 4/1971 | Mogor ...................... 128/290 |
| 3,585,104 A | 6/1971 | Kleinert |
| 3,592,194 A | 7/1971 | Duncan ..................... 128/287 |
| 3,595,235 A | 7/1971 | Jespersen ................... 128/284 |
| 3,599,388 A | 8/1971 | Feingold |
| 3,612,054 A | 10/1971 | Matsuda et al. ............ 128/287 |
| 3,677,886 A | 7/1972 | Forsshlad et al. |
| 3,700,623 A | 10/1972 | Keim .................... 260/80.3 R |
| 3,736,931 A | 6/1973 | Glassman ............... 128/290 R |
| 3,772,076 A | 11/1973 | Keim .................... 117/155 R |
| 3,836,366 A | 9/1974 | Yasui et al. |
| 3,885,158 A | 5/1975 | Flutie et al. ................ 250/440 |
| 3,886,941 A | 6/1975 | Duane et al. ............... 128/287 |
| 3,889,679 A | 6/1975 | Taylor ....................... 128/287 |
| 3,899,388 A | 8/1975 | Petrovich et al. .......... 162/164 |
| 3,901,236 A | 8/1975 | Assarsson et al. |
| 3,903,890 A | 9/1975 | Mesek et al. .............. 128/287 |
| 3,954,107 A | 5/1976 | Chesky et al. .......... 128/290 R |
| 3,972,855 A | 8/1976 | Martinsson et al. |
| 4,015,604 A | 4/1977 | Csillag ...................... 128/287 |
| 4,029,101 A | 6/1977 | Chesky et al. .......... 128/290 R |
| 4,059,114 A | 11/1977 | Richards .................... 128/287 |
| 4,062,362 A | 12/1977 | Schaar ...................... 128/287 |
| 4,069,822 A | 1/1978 | Buell ......................... 128/294 |
| 4,100,324 A | 7/1978 | Anderson et al. ........... 428/288 |
| 4,129,528 A | 12/1978 | Petrovich et al. .......... 260/823 |
| 4,144,122 A | 3/1979 | Emanuelsson et al. |
| 4,147,586 A | 4/1979 | Petrovich et al. .......... 162/135 |
| 4,200,103 A | 4/1980 | Black et al. .......... 128/290 W |
| 4,222,921 A | 9/1980 | Van Eenam .......... 260/29.6 H |
| 4,247,362 A | 1/1981 | Williams |
| 4,282,874 A | 8/1981 | Mesek |
| 4,303,471 A | 12/1981 | Laursen |
| 4,324,246 A | 4/1982 | Mullane et al. ............. 128/287 |
| 4,327,728 A | 5/1982 | Elias |
| 4,340,058 A | 7/1982 | Pierce et al. ................ 128/287 |
| 4,342,314 A | 8/1982 | Radel et al. ................ 128/287 |
| 4,351,699 A | 9/1982 | Osborn, III |
| 4,397,644 A | 8/1983 | Matthews et al. .......... 604/378 |
| 4,405,326 A | 9/1983 | Lenaghan ................... 604/385 |
| 4,410,324 A | 10/1983 | Sabee ........................ 604/368 |
| 4,432,833 A | 2/1984 | Breese |
| 4,460,642 A | 7/1984 | Errede et al. |
| 4,463,045 A | 7/1984 | Ahr et al. .................... 428/131 |
| 4,476,180 A | 10/1984 | Wnuk ........................ 428/220 |
| 4,476,323 A | 10/1984 | Hellsten et al. |
| 4,482,429 A | 11/1984 | Klowak |
| 4,482,833 A | 11/1984 | Weinert et al. |
| 4,490,147 A | 12/1984 | Pierce et al. ................ 604/378 |
| 4,522,967 A | 6/1985 | Sheldon et al. ............. 524/377 |
| 4,524,474 A | 6/1985 | Svensson ....................... 5/484 |
| 4,556,146 A | 12/1985 | Swanson et al. ............ 206/440 |
| 4,568,341 A | 2/1986 | Mitchell et al. ............ 604/368 |
| 4,573,986 A | 3/1986 | Minetola et al. ............ 604/366 |
| 4,578,070 A | 3/1986 | Holtman .................... 604/378 |
| 4,578,071 A | 3/1986 | Buell ......................... 604/379 |
| 4,589,876 A | 5/1986 | Van Tilburg ............. 604/385.1 |
| 4,594,130 A | 6/1986 | Chang et al. |
| 4,627,848 A | 12/1986 | Lassen et al. ............... 604/370 |
| 4,631,062 A | 12/1986 | Lassen et al. |
| 4,636,209 A | 1/1987 | Lassen ....................... 604/378 |
| 4,643,726 A | 2/1987 | Gegelys .................... 604/368 |
| 4,650,481 A | 3/1987 | O'Connor et al. |
| 4,654,161 A | 3/1987 | Kollmeier et al. |
| 4,655,759 A | 4/1987 | Romans-Hess et al. . 604/385 R |
| 4,657,538 A | 4/1987 | Becker et al. ............... 604/381 |
| 4,673,403 A | 6/1987 | Lassen et al. |
| 4,675,394 A | 6/1987 | Solarek et al. ................ 536/43 |
| 4,676,784 A | 6/1987 | Erdman et al. ............. 604/368 |
| 4,676,786 A | 6/1987 | Nishino ..................... 604/378 |
| 4,678,464 A | 7/1987 | Holtman ................. 604/385 R |
| 4,681,793 A | 7/1987 | Linman et al. ............. 428/138 |
| 4,687,478 A | 8/1987 | Van Tilburg ............... 604/387 |
| 4,717,498 A | 1/1988 | Maxon |
| 4,723,953 A | 2/1988 | Rosenbaum et al. ........ 604/369 |
| 4,743,245 A | 5/1988 | Lassen et al. |
| 4,753,644 A | 6/1988 | Cottenden et al. .......... 604/378 |
| 4,758,240 A | 7/1988 | Glassman |
| 4,773,905 A | 9/1988 | Molee et al. ............... 604/378 |
| 4,781,711 A | 11/1988 | Houghton et al. .......... 604/378 |
| 4,787,896 A | 11/1988 | Houghton et al. ........ 604/385.1 |
| 4,793,898 A | 12/1988 | Laamanen et al. |
| 4,795,452 A | 1/1989 | Blaney et al. ........... 604/385.1 |
| 4,804,380 A | 2/1989 | Lassen et al. |
| 4,846,824 A | 7/1989 | Lassen et al. |
| 4,865,597 A | 9/1989 | Mason, Jr. et al. |
| 4,879,170 A | 11/1989 | Radwanski et al. ......... 428/233 |
| 4,886,513 A | 12/1989 | Mason, Jr. et al. |
| 4,900,318 A | 2/1990 | Toth |
| 4,936,839 A | 6/1990 | Molee et al. ............... 604/378 |
| 4,950,264 A | 8/1990 | Osborn, III .............. 604/385.1 |
| 4,960,845 A | 10/1990 | O'Lenick, Jr. |
| 4,963,139 A | 10/1990 | Dabroski .................... 604/378 |
| 4,973,325 A | 11/1990 | Sherrod et al. ............. 604/368 |
| 4,981,557 A | 1/1991 | Bjorkquist ............... 162/168.2 |
| 4,988,344 A | 1/1991 | Reising et al. ............. 604/368 |
| 5,007,906 A | 4/1991 | Osborn, III et al. |
| 5,008,344 A | 4/1991 | Bjorkquist ............... 525/328.2 |
| 5,009,653 A | 4/1991 | Osborn, III .............. 604/385.1 |
| 5,030,229 A | 7/1991 | Yang |
| 5,030,314 A | 7/1991 | Lang |
| 5,048,589 A | 9/1991 | Cook et al. ................. 162/109 |
| 5,070,168 A | 12/1991 | O'Lenick, Jr. |
| 5,070,171 A | 12/1991 | O'Lenick, Jr. |
| 5,073,619 A | 12/1991 | O'Lenick, Jr. |
| 5,085,736 A | 2/1992 | Bjorkquist ............... 162/168.2 |
| 5,098,979 A | 3/1992 | O'Lenick, Jr. |
| 5,104,396 A | 4/1992 | Oatley et al. ............... 604/379 |
| 5,120,812 A | 6/1992 | O'Lenick, Jr. et al. |
| 5,127,911 A | 7/1992 | Baharav |
| 5,135,294 A | 8/1992 | Ohshima et al. |
| 5,147,343 A | 9/1992 | Kellenberger ............... 604/368 |
| 5,149,765 A | 9/1992 | O'Lenick, Jr. |
| 5,151,091 A | 9/1992 | Glaug et al. ............. 604/385.1 |
| 5,167,654 A | 12/1992 | Yang ....................... 604/385.2 |
| 5,171,302 A | 12/1992 | Buell ....................... 604/385.1 |
| 5,188,625 A | 2/1993 | Van Iten et al. ............. 604/383 |
| 5,190,563 A | 3/1993 | Herron et al. |
| 5,196,499 A | 3/1993 | O'Lenick, Jr. |
| 5,197,959 A | 3/1993 | Buell |
| 5,225,047 A | 7/1993 | Graef et al. |
| 5,237,035 A | 8/1993 | O'Lenick, Jr. et al |
| 5,242,435 A | 9/1993 | Murji et al. ................. 604/374 |
| 5,267,992 A | 12/1993 | Van Tilburg ............... 604/387 |
| 5,275,591 A | 1/1994 | Mavinkurve ................ 604/387 |
| 5,280,099 A | 1/1994 | Imperante et al. |
| 5,281,208 A | 1/1994 | Thompson et al. ......... 604/378 |
| 5,296,434 A | 3/1994 | Karl et al. |
| 5,300,055 A | 4/1994 | Buell |
| 5,300,358 A | 4/1994 | Evers ......................... 428/286 |
| 5,300,666 A | 4/1994 | Imperante et al. |
| 5,324,278 A | 6/1994 | Visscher et al. |
| 5,342,337 A | 8/1994 | Runeman et al. |
| 5,348,547 A | 9/1994 | Payne et al. ................ 604/378 |
| 5,348,620 A | 9/1994 | Hermans et al. |
| 5,350,624 A | 9/1994 | Georger et al. ............. 428/219 |

| | | | | | | |
|---|---|---|---|---|---|---|
| 5,356,405 A | 10/1994 | Thompson et al. ......... 604/384 | | 5,843,852 A | 12/1998 | Dutkiewicz et al. |
| 5,360,422 A | 11/1994 | Brownlee et al. ........ 604/385.2 | | 5,851,648 A | 12/1998 | Stone et al. |
| 5,399,175 A | 3/1995 | Glaug et al. ............. 604/385.1 | | 5,855,572 A | 1/1999 | Schmidt |
| 5,399,412 A | 3/1995 | Sudall et al. ............... 428/153 | | 5,858,011 A | 1/1999 | Brown et al. |
| 5,401,267 A | 3/1995 | Couture-Dorschner et al. .......................... 604/384 | | 5,858,021 A | 1/1999 | Sun et al. |
| | | | | 5,865,824 A | 2/1999 | Chen et al. ................. 604/378 |
| 5,405,342 A | 4/1995 | Roessler et al. ............ 604/364 | | 5,866,242 A | 2/1999 | Tan et al. |
| 5,423,786 A | 6/1995 | Fung et al. ................. 604/367 | | 5,883,231 A | 3/1999 | Achter et al. |
| 5,429,629 A | 7/1995 | Latimer et al. ............. 604/378 | | 5,888,345 A | 3/1999 | Knapick et al. |
| 5,429,686 A | 7/1995 | Chiu et al. .............. 139/383 A | | 5,914,125 A | 6/1999 | Andrews et al. |
| 5,460,623 A | 10/1995 | Emenaker et al. .......... 604/368 | | 5,935,383 A | 8/1999 | Sun et al. |
| H1511 H | 12/1995 | Chappell et al. ............ 604/383 | | 5,990,377 A | 11/1999 | Chen et al. |
| 5,484,430 A | 1/1996 | Osborn, III .............. 604/385.1 | | 6,015,648 A | 1/2000 | Mitsumura et al. |
| 5,489,469 A | 2/1996 | Kobayashi et al. | | 6,020,055 A | 2/2000 | Pearce |
| 5,490,846 A | 2/1996 | Ellis et al. .................. 604/366 | | 6,020,536 A | 2/2000 | Osterdahl et al. |
| 5,509,913 A | 4/1996 | Yeo ............................ 604/364 | | 6,103,953 A | 8/2000 | Cree et al. |
| 5,509,914 A | 4/1996 | Osborn, III | | 6,165,306 A | 12/2000 | Rajala |
| 5,514,104 A | 5/1996 | Cole et al. .................. 604/366 | | 6,172,276 B1 | 1/2001 | Hetzler et al. |
| 5,522,809 A | 6/1996 | Larsonneur ................. 604/361 | | 6,198,019 B1 | 3/2001 | Hansson et al. |
| 5,527,300 A | 6/1996 | Sauer .......................... 604/378 | | 6,326,525 B1 | 12/2001 | Hamajima et al. |
| 5,533,991 A | 7/1996 | Kirby et al. ................ 604/383 | | 6,328,724 B1 | 12/2001 | Ronnberg et al. |
| H1585 H | 8/1996 | Ahr ............................ 604/378 | | 6,503,233 B1 * | 1/2003 | Chen et al. ............ 604/385.01 |
| 5,545,156 A | 8/1996 | DiPalma et al. ......... 604/385.1 | | | | |
| 5,558,656 A | 9/1996 | Bergman ................. 604/385.1 | | FOREIGN PATENT DOCUMENTS | | |
| 5,562,645 A | 10/1996 | Tanzer et al. ............... 604/367 | DE | 32 05 931 A1 | 9/1983 | ........... A41B/13/02 |
| 5,562,650 A | 10/1996 | Everett et al. .............. 604/378 | EP | 0 124 365 A1 | 11/1984 | ........... A61F/13/00 |
| H1614 H | 11/1996 | Mayer et al. ............ 604/385.1 | EP | 0 136 524 A1 | 4/1985 | ........... A61F/13/18 |
| 5,575,786 A | 11/1996 | Osborn, III ................ 604/387 | EP | 0 225 940 A1 | 6/1987 | |
| 5,578,025 A | 11/1996 | May | EP | 0 360 285 A2 | 3/1990 | |
| 5,591,148 A | 1/1997 | McFall et al. .............. 604/378 | EP | 0 366 079 A2 | 5/1990 | |
| 5,591,150 A | 1/1997 | Olsen et al. ............. 604/385.1 | EP | 0 374 910 B1 | 6/1990 | |
| 5,595,628 A | 1/1997 | Gordon et al. | EP | 0 395 223 A2 | 10/1990 | |
| 5,599,337 A | 2/1997 | Mccoy .................... 604/385.1 | EP | 0 441 064 A1 | 8/1991 | |
| 5,603,707 A | 2/1997 | Trombetta et al. .......... 604/383 | EP | 0 391 727 A2 | 10/1991 | |
| 5,607,551 A | 3/1997 | Farrington, Jr. et al. .... 162/109 | EP | 0 483 592 A1 | 5/1992 | |
| 5,611,790 A | 3/1997 | Osborn, III et al. ........ 604/391 | EP | 0 549 784 B1 | 7/1993 | ........... A61F/13/15 |
| 5,613,964 A | 3/1997 | Grenier | EP | 0 552 345 B1 | 9/1993 | |
| 5,624,423 A | 4/1997 | Anjur et al. ............. 604/385.1 | EP | 0 597 273 A1 | 5/1994 | |
| 5,643,238 A | 7/1997 | Baker ......................... 604/368 | EP | 0 682 927 A1 | 11/1995 | |
| 5,643,653 A | 7/1997 | Griesbach, III et al. .... 428/120 | EP | 0 687 453 A1 | 12/1995 | |
| 5,647,863 A | 7/1997 | Hammons et al. .......... 604/378 | EP | 0 781 537 A1 | 2/1997 | ........... A61F/13/00 |
| 5,649,916 A | 7/1997 | DiPalma et al. ............ 604/378 | EP | 0768 070 A1 | 4/1997 | ........... A61F/13/00 |
| 5,662,633 A | 9/1997 | Doak et al. ................. 604/378 | EP | 0 768 072 A1 | 4/1997 | ........... A61F/13/15 |
| 5,672,248 A | 9/1997 | Wendt et al. ................ 162/109 | EP | 0 804 913 A1 | 11/1997 | ........... A61F/13/15 |
| 5,681,303 A | 10/1997 | Mills et al. ............... 604/385.2 | EP | 0 875 224 A1 | 11/1998 | |
| 5,688,259 A | 11/1997 | Osborn, III et al. ...... 604/385.1 | EP | 0 893 517 A2 | 1/1999 | |
| 5,692,939 A | 12/1997 | DesMarais .................. 442/373 | EP | 0 904 755 A2 | 3/1999 | |
| 5,695,487 A | 12/1997 | Cohen et al. ............... 604/384 | FR | 1358269 | 12/1964 | |
| 5,702,378 A | 12/1997 | Widlund et al. | FR | 1554951 | 1/1969 | |
| 5,711,970 A | 1/1998 | Lau et al. | GB | 2 233 235 A | 1/1991 | |
| 5,725,821 A | 3/1998 | Gannon et al. | GB | 2 296 437 B | 7/1996 | ........... A61F/13/15 |
| 5,741,241 A | 4/1998 | Guidotti et al. | GB | 2 319 730 | 6/1998 | |
| 5,746,732 A | 5/1998 | Olsson et al. ............ 604/385.2 | TW | 335346 | 7/1998 | |
| 5,752,947 A | 5/1998 | Awolin ....................... 604/387 | WO | WO 83/03051 | 9/1983 | |
| 5,755,710 A | 5/1998 | Menard | WO | WO 92/07535 A1 | 5/1992 | |
| 5,766,213 A | 6/1998 | Hackman et al. | WO | WO 92/07535 | 5/1992 | |
| 5,769,835 A | 6/1998 | Fell et al. ................ 604/385.2 | WO | WO 96/17573 A3 | 6/1996 | |
| 5,772,845 A | 6/1998 | Farrington, Jr. et al. | WO | WO 96/38232 A1 | 12/1996 | ........... B05D/3/02 |
| 5,779,860 A | 7/1998 | Hollenberg et al. ......... 162/206 | WO | WO 97/14389 A1 | 4/1997 | ........... A61F/13/15 |
| 5,792,129 A | 8/1998 | Johansson et al. .......... 604/387 | WO | WO 97/21453 A1 | 6/1997 | |
| 5,792,130 A | 8/1998 | Widlund et al. ......... 604/385.1 | WO | WO 97/34558 A1 | 9/1997 | ........... A61F/13/15 |
| 5,795,345 A | 8/1998 | Mizutani et al. | WO | WO 97/34559 A1 | 9/1997 | ........... A61F/13/46 |
| 5,795,377 A | 8/1998 | Tanner et al. | WO | WO 98/00081 A1 | 1/1998 | ........... A61F/13/15 |
| 5,795,921 A | 8/1998 | Dyer et al. | WO | WO 98/00082 A1 | 1/1998 | ........... A61F/13/15 |
| 5,800,417 A | 9/1998 | Goerg-Wood et al. | WO | WO 98/01684 A1 | 1/1998 | |
| 5,807,365 A | 9/1998 | Luceri .................... 604/385.1 | WO | WO 98/24389 A1 | 6/1998 | ........... A61F/13/15 |
| 5,807,367 A | 9/1998 | Dilnik et al. ............... 604/369 | WO | WO 98/31318 | 7/1998 | |
| 5,810,798 A | 9/1998 | Finch et al. | WO | WO 98/36720 A1 | 8/1998 | |
| 5,817,079 A | 10/1998 | Bergquist et al. | WO | WO 98/43684 A1 | 10/1998 | |
| 5,824,004 A | 10/1998 | Osborn, III et al. | WO | WO 00/62730 A1 | 10/2000 | |
| 5,837,184 A | 11/1998 | Firgo et al. | WO | WO 00/63487 A1 | 10/2000 | |

OTHER PUBLICATIONS

American Society for Testing Materials (ASTM) Designation: D 4032–82, "Standard Test Method for Stiffness of Fabric by the Circular Bend Procedure," pp. 702–706, published Aug. 1982.

American Society for Testing Materials (ASTM) Designation: D 3574–91, "Standard Test Methods for Flexible Cellular Materials—Slab, Bonded, and Molded Urethane Foams," Procedures C and H, published Mar. 1992.

Chatterjee, P.K., Editor, Absorbency, published by Elsevier, 1985, pp. 42–44.

Dullien, F. A. L., Porous Media: Fluid Transport and Pore Structure, Academic Press, New York, 1979, pp.78–83.

Federal Specifications UU–T–595b, "Towel, Wiping, Paper: Industrial And Institutional," Apr. 4, 1967, 8 pages.

Federal Specification UU–T–595c, "Towel, Wiping, Paper: Industrial And Institutional," Jul. 27, 1976, 8 pages.

Kallmes, O.J. et al., "The Gravimetric Absorbency Testing System (GATS)," Tappi Symposium —1985 Nonwoven Symposium, pp. 231–235.

Patent Cooperation Treaty Search Report from the International Search Authority, International Application No. PCT/US 99/22168 dated Mar. 29, 2000.

American Society for Testing Materials (ASTM) Designation: D 1921–89, "Standard Test Methods for Particle Size (Sieve Analysis) of Plastic Materials," published Aug. 1989.

American Society for Testing Materials (ASTM) Designation: D 6128–97, "Standard Shear Testing Method for Bulk Solids Using the Jenike Shear Cell," published Oct. 1998.

Austin, L.G. et al., "Size Reduction of Solids: Crushing and Grinding Equipment," Chapter 12 in *Handbook of Powder Science and Technology*, 2nd edition, Chapman & Hall, New York, 1997, pp. 586–634.

Disapio, Alfred J. et al., "Microporous Macrobeads Provide New Opportunities in Skin Care," *Soap & Cosmetics*, vol. 75, No. 2, Feb. 1999, pp. 42–44,46–47.

Hostetter, David W., "Comparing Kneading and Disk Dispersion," *PaperAge*, Nov. 1995, p.16.

Kayne, Brian H., "Mixing of Powders," Chapter 11 in *Handbook of Powder Science & Technology*, 2nd edition, Chapman & Hall New York, 1997, pp. 568–585.

Main, Steve et al., "Retention Aids for High–Speed Paper Machines," *Tappi Journal*, vol. 82, No. 4, Apr. 1999, pp. 78–84.

O'Lenick Jr., Anthony J. et al., "Silicone Compounds: Not Just Oil Phases Anymore," *Soap/Cosmetics/Chemical Specialties*, Jun. 1998, pp. 55–57.

Rahn, K. et al., "New Cellulosic Polymers By Subsequent Modification of 2,3–Dialdehyd Cellulose," *Cellulose Chemistry and Technology*, vol. 32, 1998, pp. 173–183.

Shinohara, Kunio, "Fundamental and Rheological Properties of Powders," Chapter 4 in *Handbook of Powder Science & Technology*, 2nd edition, Chapman & Hall, New York, 1997, pp. 96–145.

\* cited by examiner

ABSORBENT ARTICLE HAVING GOOD BODY FIT UNDER DYNAMIC CONDITIONS

PRIORITY

This application is a continuation of U.S. application Ser. No. 09/165,871, filed Oct. 2, 1998, now U.S. Pat. No. 6,503,233 issued Jan. 7, 2003.

BACKGROUND OF THE INVENTION

In the art of absorbent articles, there is a need for articles with improved body fit. For sanitary napkins in particular, advances in absorbent materials and covers may offer relatively little benefit in actual use if the fluid from the user does not reach the intended intake regions of the article. A significant gap between the body and the intake area of the pad can result in fluid traveling along the body to stain clothing. Further, fluid on the body will not be effectively removed, resulting in a wet, unclean feeling.

Many efforts have been made to improve body fit. Three-dimensional articles have been proposed with fluff pulp, foams or other bulky elements creating a thick central region of the pad designed to fit female anatomy while in use. However, such articles are bulky, resulting in high cost and inconvenience since a relatively small number of articles can be fit into a pad. Further, interviews with women have indicated a preference for articles that appear relatively thin and flat versus three-dimensional "pre-shaped" articles. Further, a pre-shaped article having a fixed shape and size may not adapt well to the wide variety of dimensions that exist among females.

Flexure-resistant deformation elements have been used in an attempt to force an absorbent article to fold into a W-shape when compressed laterally. A limitation typically found in this approach is that the deformation elements are located on the garment side of the article, forcing the entire absorbent core to deflect upward and experience a degree of vertical compression which can reduce the void volume in the article as worn. The stiffness required for shaping induced by a garment-side element can also lead to discomfort when worn. Further, the flexure-resistant deformation elements can add to the cost and complexity of the article, often without increasing the absorbent capacity.

Recently, efforts have been made to create channels, especially embossed channels, in a pad to influence the way a pad deforms when compressed by the legs of the wearer, striving to induce an upward buckling of the central portions of the absorbent core to contact the body. However, some of the absorbent core in the central regions of the article may also be deflected downward, away from the body, especially when multilayered absorbent cores are used, and control of the folding mechanism in general is weak when relying on the influence of embossed side channels. In some cases, folding of the central portions of the absorbent core may be downward, away from the body, resulting in inefficient intake.

Further, prior attempts to improve body fit with embossed arcuate lines may adversely affect fluid handling by permitting fluid flow along the embossed lines toward the edges of the article, where leakage may occur. Generally, such arcuate embossments are outwardly concave, with the longitudinal ends of the embossments being near the outer perimeter of the absorbent core and the longitudinal midpoint of the embossments being relatively closer to the longitudinal centerline than the ends of the embossments. Such outwardly concave arcuate lines are believed to be useful in reducing stiffness and improving body fit, but they may provide channels with low absorbency through which fluid can flow from the center of the pad toward the longitudinal sides of the article.

Wings and tabs have also been added to help promote folding of the article in use to direct the central portion toward the body in a W-shaped geometry, but these also do not provide direct control over the folding geometry, especially in the center of the pad. In general, none of these previous efforts have been fully successful in promoting direct contact of the pad with the body under typical conditions of use.

A particular problem with past efforts for improved body fit is that strategies to raise the central portion of the pad in use, such as expanding foams or embossed side channels, tend to be incompatible with the fit requirements for regions of the pad away from the target area. Ideally, an initially flat pad, when laterally compressed in the crotch region, will assume a W-fold geometry in the center of the pad and will cause the back and ends of the pad to curl upward to fit the body or at least will not encourage those regions to move away from the body. But when known pads are laterally compressed in a way to promote a central W-fold, the front and ends of the article do not curl up and the longitudinal sides of the article in the front and the back may curl downward.

What is needed is an improved structure that increases the likelihood of body contact with the intended intake region of the absorbent core, while also providing good fluid handling, leakage protection and comfort.

SUMMARY OF THE INVENTION

It has been discovered that an absorbent article can be relatively flat and yet deform when compressed laterally to give good body fit throughout its length, having, for example, a W-fold geometry substantially limited to the crotch region while also inducing longitudinal upward curt in the front and back regions of the absorbent article, thus giving it an excellent geometry for body fit in sanitary napkins, incontinence pads, and other absorbent articles for use on the body. It has also been discovered that crease lines for promoting downward folding coupled with a shaping line (or multiple shaping lines) for promoting upward folding of portions of the absorbent core can be used to achieve good body fit, offering good control over the upward deflection of a central absorbent member in the absorbent core of the article during lateral compression. Further, it has been discovered that a combination of crease lines and a shaping line in an absorbent core can provide improved fluid handling properties and leakage control in addition to assisting the body-fitting function of an absorbent article, particularly when a wicking barrier is used to separate two distinct members of the absorbent core and permit relative motion of the members during compression.

Hence, in one aspect, the present invention resides in an absorbent article having a crotch region and a body side, the absorbent article comprising:
  a) a liquid impervious backsheet;
  b) a liquid pervious topsheet attached to the backsheet;
  c) an absorbent core positioned between the topsheet and the backsheet, the absorbent core comprising an outer absorbent member and a central absorbent member, the outer absorbent member having a width in the crotch region greater than the width of the central absorbent member in the crotch region, the absorbent core further comprising at least two crease lines outside the central absorbent member and a shaping line in the central absorbent member.

In another aspect, the invention resides in an absorbent article, the article having a crotch region, a body side, and a garment side, the absorbent article comprising:

a) a liquid impervious backsheet;

b) a liquid pervious topsheet attached to the backsheet;

c) an absorbent core positioned between the topsheet and the backsheet, the absorbent core comprising an upper layer toward the body side and a lower layer toward the garment side, the upper layer comprising a shaping line and the absorbent core further comprising crease lines substantially not within the upper layer; and d) a polymeric web disposed between the upper layer and lower layer of the absorbent article.

In another aspect, the invention resides in an absorbent article having a longitudinal direction, a transverse direction, a vertical direction substantially normal to both the longitudinal and transverse directions, and a body side, the absorbent article comprising:

a) an absorbent core having a body side surface, the absorbent core comprising an outer absorbent member having a central void open toward the body side of the article, and a central absorbent member disposed over the central void of the outer absorbent member and extending at least partially into the void, the central absorbent member comprising a shaping line; and b) a wicking barrier disposed between the outer absorbent member and the central absorbent member, the wicking barrier comprising a vertical component spanning a vertical distance between the outer absorbent member and the central absorbent member.

In still another aspect, the invention resides in an absorbent article with a crotch region, a longitudinal direction, a transverse direction, and a vertical direction substantially normal to both the longitudinal and transverse directions, the absorbent article comprising:

a) an absorbent core having a central absorbent member and an outer shaping member, the central absorbent member comprising a shaping line, the outer shaping member having a central void defined therein for receiving at least a portion of the central absorbent member, whereby an interface is defined between the central absorbent member and the outer shaping member, the interface spanning a vertical distance, and b) a wicking barrier disposed along the interface between the central absorbent member and the outer absorbent member.

DETAILED DESCRIPTION OF THE INVENTION

Figure 1:
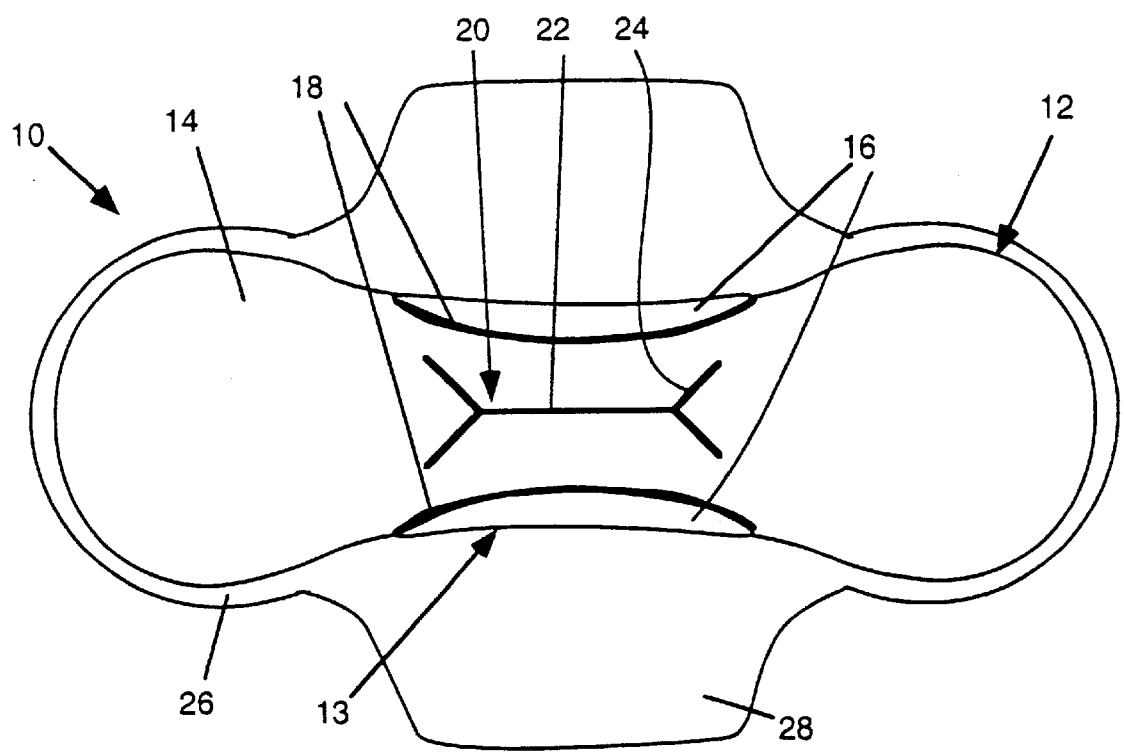
FIG. 1 is a top view of an sanitary napkin with wings comprising crease lines and shaping lines according to the present invention.

A central absorbent member, when properly treated to have a shaping line or lines for upward deflection, coupled with an outer or underlying absorbent member that comprises crease lines for downward deflection, can serve together as a body-conformable absorbent core in an absorbent article. During lateral compression, as occurs between the thighs of a wearer of a sanitary napkin, the deflection along the crease lines produces valleys that can help retain and distribute fluid, while the shaping lines in the central portion of the article help induce upward deflection in the crotch region or other selected regions to achieve the desired degree of body conformability.

Desirably, the central absorbent member and outer absorbent member are separated at least partially to provide a degree of independent motion of the central absorbent member and outer absorbent member. Polymeric barriers or other flexible elements between the central absorbent member and outer absorbent member of the article can be especially beneficial in promoting independent deformation of the respective members to achieve good body fit.

As used herein, the word "line" or "lines" in the terms "shaping line" and "crease lines" refer to narrow, elongated sections that promote folding by providing a sudden change in material properties of matter along the line relative to matter on either side of the line. A line can be straight, arcuate, sinusoidal, wavy, angular, or zig-zag-like, and can have multiple elements, such as a line that extends longitudinally followed by a bend or turn toward the center of the article, or can be a series of short segments that define a line. A shaping line or crease line may also be comprised of a series of dots, such as dots formed by adhesives or heat and pressure to create densified, bonded spots spaced apart to define a line. Lines may have a width less than about 10 millimeters (mm), desirably less than about 5 mm, more specifically less than about 3 mm, and most specifically between about 0.5 mm and about 2 mm. Since a shaping line will generally have multiple components, such as longitudinal portions and outwardly spanning segments, the terms "shaping lines" and "shaping line" can generally be used interchangeably.

In the absorbent articles of the present invention, the absorbent core comprises at least two sets of lines, crease lines and shaping lines, that define how the absorbent core will fold, deform, bend, or deflect when compressed laterally in the crotch region such as by the legs of a user or when the longitudinal sides of the article in the crotch region are gripped by human fingers and moved inwardly, each longitudinal side moving in a common plane toward the opposing side. During such compression, it is desired that an essentially W-shaped fold be established in the crotch region due to deflection of the absorbent core. As used herein, a "W-shaped fold" in the absorbent article means that the cross-section of the laterally compressed article along or near the transverse centerline of the article shows a shape approximated by the letter W, with outer valleys around a central mound. The central mound may be rounded, relatively flat at the top, or sharp like an inverted V. In one embodiment, a gap is created between a central absorbent member and an outer absorbent member during lateral compression in the crotch region.

A W-shaped fold can be produced with simple lateral compression by proper placement of crease lines and a shaping line or lines. Specifically, the absorbent core comprises at least two crease lines, typically a pair of crease lines, generally symmetrically placed on both sides of the longitudinal axis of the article, which induce, promote, or permit downward folding of the absorbent core at or near the crease lines during lateral compression to produce "valleys" (generally downward cusps or V-shaped deflections relative to the transverse direction of the absorbent core). Typically, the crease lines are located outside the central absorbent member of the absorbent core of an absorbent article. Downward folding along the crease lines is typically associated with upward folding of the longitudinal sides of the article. The crease lines are coupled with a shaping line or shaping lines closer to the longitudinal axis of the article than the crease lines, typically located in the central absorbent member of the absorbent core of an absorbent article, wherein the shaping line promotes or permits upward folding of the central region of the absorbent core during lateral compression to provide good body fit. The shaping line, closer to the longitudinal centerline of the article than the crease lines, is designed to translate lateral compression into vertical deflection (upward protrusion) of a central region of the absorbent article, resulting, for example, in an upward mound, particularly when combined with the downward deflection (downward depression) of the article along the crease lines. Thus, during lateral compression in the crotch region of an absorbent article, the shaping line promotes bending or deflecting of a central absorbent member toward the body side of the absorbent article in the crotch region while the crease lines promote bending or deflecting of the absorbent article and, in one embodiment, an outer absorbent member, away from the body side of the absorbent article in the crotch region. The shaping line helps direct the upward motion of the central region of the absorbent article and guide not only the shape of the upward deflection, by influencing how the article folds and deforms when compressed laterally, but also guides the longitudinal extent of the upward fold.

Without wishing to be bound by theory, it is believed that the natural curvature of panties and the shaping induced by elastics therein will tend to force the outward edges of a sanitary napkin to be at a slight angle relative to horizontal (usually less than 90 degrees) such that the outward edges of the article are higher than the crease lines, thus naturally promoting formation of downward valleys along the crease lines. Initial formation of downward valleys at the crease lines is believed to then promote natural upward (toward the body) deformation of the central absorbent member during subsequent lateral compression. The angled outer portions of the absorbent article can then act to shove or push the central absorbent member upward as the outer portions of the article are pushed laterally inward by compression from the user's thighs, particularly if the crease lines are sufficiently flexible and if the shaping lines are in place. From this perspective, the crease lines suitably can be substantially more flexible or more easily folded than the shaping lines, such that the crease lines form valleys first and then, once that geometry has been established, the shaping lines can then deform under subsequent lateral compression to provide the desired upward folding in the central absorbent member. However, in some embodiments the shaping line or lines can also be more flexible than the crease lines.

Desirably, the upward mound, created near the longitudinal centerline of the article by the upward motion of the central regions of the absorbent article as directed by the shaping lines, does not persist throughout the length of the article, but, as influenced by the shaping lines, terminates just outside the crotch region to permit the article to better conform to the regions outside the crotch area, where an inverted V-shape may be useful in the rear of the article to better conform to the buttocks, and where the article generally should be relatively flat in the transverse direction and curled concave up in the longitudinal direction for best body fit in the front of the pad. Proper shaping of regions outside the crotch region during lateral compression can be achieved by providing additional slits, reinforcing elements, elastic components, or attachment elements to the absorbent core.

Desirably, the shaping of the article during compression is influenced by crease lines and shaping lines in the absorbent core itself without the need for an additional deformation element, and particularly without the presence of a flexure-resistant deformation element beneath the central absorbent member or without the presence of a flexure-resistant deformation element beneath the absorbent core. Also desirably, the central portion of the absorbent article is substantially free of non-absorbent elements, apart from the topsheet, the backsheet, an optional baffle layer or wicking barrier beneath the central absorbent member, and a small quantity of adhesive for product attachment and integrity.

For best results, it may be necessary or helpful in some embodiments that the user flex the absorbent article slightly upon attachment to the panties of the user when placing the absorbent article in contact with the body to ensure that the central absorbent member deflects upward and that the crease lines deflect downward to provide valleys. Generally, an article can be considered to successfully flex into a W-shape if at least 60% of women who wear the article find that a W-shape is achieved and maintained in use. Preferably, at least 75% of users should find that a W-fold geometry is achieved and maintained in use when the article is properly attached and worn.

In one exemplary embodiment, the absorbent article comprises one or more layers of absorbent material with outwardly concave arcuate crease lines in the crotch region formed by embossing the absorbent material near the longitudinal sides of the article, further comprising a central shaping line formed by perforating or notching the absorbent material in the central region of the pad, the shaping lines having a geometry similar to a double headed arrow with reverse arrow heads, or ">-<", centered along the longitudinal centerline of the article between the crease lines, and with the longitudinal axis of the arrow aligned with the longitudinal axis of the article. Such a geometry for the shaping line permits the central region of the absorbent core between the outward "arrow heads" to deflect upward while downward deflection occurs along the crease lines. Another successful geometry for the shaping line is a pair of outwardly concave arcuate lines whose midpoints touch or approach each other, longitudinally aligned and substantially symmetrically placed about both sides of the longitudinal axis in the crotch region between the outer crease lines, and desirably smaller in length than the crease lines. Such arcuate crease lines resemble the shape of a right and left parentheses placed back to back, or ")(", with the vertical axis of the parentheses substantially aligned with the longitudinal axis of the article. Likewise, the shaping line in many embodiments can be described as convex toward the longitudinal centerline of the article and generally contained within the absorbent core and specifically generally contained within the central absorbent member.

Likewise, the shaping line can comprise a longitudinal central line comprising two endpoints and, near both of the endpoints, a pair of outwardly spanning lines having inner and outer endpoints, wherein each inner endpoint is both relatively nearer the longitudinal centerline and relatively nearer the transverse centerline than the corresponding outer endpoint. Alternatively, the outwardly spanning lines can have inner and outer endpoints, wherein each inner endpoint is relatively nearer the longitudinal centerline and relatively further away from the transverse centerline than the corresponding outer endpoint. Generally, the shaping line comprises a central longitudinal portion and outwardly spanning sections which traverse a substantial distance from the vicinity of the longitudinal centerline to the vicinity of the longitudinal edge of the central absorbent member. Similarly, the shaping line in several embodiments can comprise longitudinal components near the centerline and additional oblique components (oblique relative to the longitudinal centerline of the article). The outward spanning lines may extend into the outer absorbent member as well, either extending outward past the longitudinal sides of the central absorbent member or extending vertically into the depth of any underlying portion of the outer absorbent member. Desirably, in some embodiments, the shaping line comprises oblique elongated zones of reduced strength spanning a transverse distance between the longitudinal centerline of the article and the longitudinal sides of the central absorbent member of at least about 2 mm, more specifically at least about 3 mm, more specifically still at least about 5 mm, with exemplary ranges of about 4 mm to about 10 mm or from about 5 mm to about 15 mm. When linear, oblique outwardly-spanning lines can form a minimum angle of about 20 degrees or greater relative to the longitudinal centerline, more specifically about 30 degrees or greater, more specifically still about 40 degrees or greater, and most specifically about 45 degree or greater, with an exemplary range of from about 25 degrees to about 90 degrees.

The shaping line or crease lines of the absorbent article can generally be created in any way likely to guide the folding of a flexible material having a degree of intrinsic stiffness such as an air laid pad, a mat of fluff pulp, a stack of tissue layers, a web of coform material or other fiber-polymer composites, or a high-loft nonwoven web. The shaping line or crease lines desirably are produced by one of more treatment methods such as embossing, stamping, or other known methods for creating densified regions; slitting; cutting; notching; tearing; thermobonding (application of heat to create bonding, particularly with thermoplastic materials or heat-setting resins); hot pressing (simultaneous application of heat and pressure, especially in conjunction with thermoplastic binder materials, thermosetting plastics, or heat setting resins); ultrasonic bonding; perforating; perf-embossing; needling; impregnation by resins, waxes, or thermoplastics; hydraulic cutting by water jets or other fluid jets; pre-folding; creasing; scoring; or removing material by abrasion, ablation, picking, scraping, or suction. In certain embodiments, then, the crease lines and shaping lines may be a series of perforations, notches, cuts, tears, or slits optionally having portions not fully perforated, notched, cut, torn, or slit along a line's length for increased integrity. Crease lines and shaping lines formed by slitting or creation of densified areas are believed to be especially useful due to their ease of application and general effectiveness.

Crease lines and shaping lines can also be created by bonding a portion of the cover or backsheet to a compressed portion of the absorbent material using the methods described by Mogor in U.S. Pat. No. 3,575,174, issued Apr. 20, 1971, herein incorporated by reference in its entirety. The articles of the present invention can also comprise embossments in the back region of the article to promote an inverted V-shape fold in the rear of the article for more comfortable article placement between the buttocks of a user.

Treatment methods for creating a shaping line or crease lines are applied to make a distinct line differing in material properties from the surrounding material in a manner that promotes folding at or near the treated line during lateral compression of the article. Material properties that may be modified to encourage such folding can include density, stiffness, basis weight, tensile strength, chemical composition (e.g., resins and fibers versus fibers alone), and internal integrity or bond strength (especially z-direction bond strength). A line can be a gap or void space between absorbent members, wherein the line has a material property, for example, of zero basis weight relative to the surrounding non-zero basis weight regions.

For a shaping line comprising outward spanning lines, it is preferred that the outward spanning lines be made in a manner that reduces the bending stiffness or tensile strength of the central absorbent member along the outward spanning line. Useful methods for reducing bending stiffness or tensile strength along a shaping mine (or crease line) include slitting, cutting, perforating, scoring, notching, removal of material (e.g., mechanical picking, abrasion, laser etching, scraping, blasting with air jets), needling, chemical debonding (e.g., application of chemicals along the line that debond fibers or attack existing bonds) and initial formation with reduced basis weight. Slitting of outward spanning lines in a shaping line (or portions of a shaping line that effectively serve as outward spanning lines, such as the end portions of an arc) is especially desirably in some embodiments where a gap beneath the elevated central absorbent member is desired, for slit-outward spanning lines can permit a central portion of the central absorbent member to deflect upwards while leaving the portions of the central absorbent member toward the longitudinal ends thereof to remain flat or curved longitudinally upwards. As a result, there is a sudden vertical change in height about the outward spanning lines, leaving a gap or void space open to receive fluid beneath the upwardly deflected portion of the central absorbent member. Slit outward spanning lines may be at one or both ends of the collection of shaping lines in the central absorbent member, yielding one or two gaps or void spaces, respectively, into which fluid can flow beneath the upwardly deflected portion of the central absorbent member, and generally resulting in an increase of void volume within the absorbent article.

The length spanned by the shaping line or lines in the longitudinal direction can be at least about 1 cm, specifically at least about 2 cm, more specifically from about 3 cm to about 10 cm, more specifically still from about 4 cm to about 8 cm, and most specifically from about 4 cm to about 6 cm. In sanitary napkins and other absorbent articles, a longitudinal slit or notch, if present, desirably can be from about 4 cm to about 6 cm long. The longitudinal length of the crease lines can be smaller than that of the shaping lines, but in most embodiments desirably is about the same as or longer than that of the shaping line. For example, the crease lines can be longer than the shaping lines in the longitudinal direction by at least about 1 cm, more specifically at least about 2 cm, more specifically at least about 3 cm, and most specifically from about 2.5 cm to 5 cm.

The absorbent core generally comprises two primary sections, a central absorbent member and an outer absorbent member (or, in some embodiments, an outer shaping member, described below). The absorbent material of the central absorbent member and/or the outer absorbent member can be any absorbent material known in the art of personal care articles and absorbent articles. The outer absorbent member can be substantially planar and reside below the central absorbent member, or it can be provided with a central void or depression therein which can at least partially receive the central absorbent member such that an interface is established between the two sections that spans a finite vertical distance. Desirably, the central absorbent member has at least one in-plane dimension smaller than the corresponding dimension of the outer absorbent member. Generally, the transverse width of the central absorbent member will be less than the transverse width of the outer absorbent member at least in the crotch region. Thus, in one embodiment, the outer absorbent member will have a width in the crotch region that is greater than the width of the central absorbent member in the crotch region.

In one embodiment of the present invention, the central absorbent member further comprises first and second longitudinal sides, wherein at least one crease line is located substantially along a portion of the first longitudinal side of the central absorbent member such that, during lateral compression in the crotch region, a valley having first and second sides is formed along a portion of the first longitudinal side of the central absorbent member, wherein the first side of the valley comprises a portion of the outer absorbent member and the second side of the valley comprises a portion of the central absorbent member.

The absorbent materials of the absorbent core, including either the central absorbent member or the outer absorbent member or both, can comprise one or more plies of wetlaid or airlaid tissue; cellulosic airlaid webs of comminuted fibers (commonly termed "fluff" or "airfelt"); other dry laid webs; cellulose-superabsorbent mixtures or composites; hydroentangled webs comprising cellulosic fibers; composites of syhthetic fibers and papermaking fibers; cellulosic foams including regenerated cellulose-foams; hydrophilic flexible foams; fiber-foam composites; absorbent nonwoven webs; the foam-structured fibrous absorbent materials of F.-J. Chen et al. disclosed in the commonly owned, copending U.S. patent application "Fibrous Absorbent Material and Methods of Making the Same," Ser. No. 09/083,873, filed May 22, 1998, herein incorporated by reference; or absorbent foams produced from high internal phase emulsions, such as the foams disclosed in U.S. Pat. No. 5,692,939, issued Dec. 2, 1997 to DesMarais, herein incorporated by reference.

A commercially available air-laid web is AIRTEX™ 395 air-laid web sold by Fort James Corporation located in Green Bay, Wis. AIRTEX 395 air-laid web is essentially 100 percent virgin softwood held together by an acrylic binder. Concert Fabrication Ltee, of Ontario, Canada, also produces a variety of densified airlaid webs held together with thermoplastic binder material.

A particularly useful cellulose-polymer composite material is coform, a hydraulically entangled mixture of pulp fibers and polymer, such as the materials disclosed in U.S. Pat. No. 4,879,170, issued Nov. 7, 1989 to Radwanski et al.; U.S. Pat. No. 4,100,324 to Anderson et al. and U.S. Pat. No. 5,350,624 to Georger et al., the contents of which are incorporated herein by reference in their entireties.

The absorbent materials of the absorbent core can also comprise corrugated absorbent materials for enhanced longitudinal transport of fluid, such as the materials disclosed in U.S. Pat. No. 4,578,070, issued Mar. 25, 1986 to Holtman, herein incorporated by reference in its entirety. The absorbent core can also comprise regenerated cellulose foam. Desirably, the outer absorbent member or the central absorbent member comprises densified fluff pulp, stabilized air laid pulp, coform, or the soft pulp sheets disclosed in U.S. Pat. No. 5,562,645, issued Oct. 8, 1996 to Tanzer et al., herein incorporated by reference in its entirety. The density of either the central absorbent member or outer absorbent member (or shaping member) of the absorbent core can be less than about 0.3 grams per cubic centimeter (g/cc) and more specifically less than about 0.2 g/cc, and most specifically between about 0.03 g/cc and about 0.15 g/cc. Excessively low densities may lack the degree of stiffness required for effective folding and shaping of the article during lateral compression.

Any suitable form of cellulosic material can be incorporated in the absorbent materials of the absorbent core, including wood fibers, such as bleached kraft softwood or hardwood, high yield wood fibers, and chemithermomechanical pulp fibers; bagasse; milkweed; wheat straw; kenaf; hemp; or peat moss. The fibers can also be crosslinked, sulfonated, mercerized, heat treated, mixed with thermoplastic stabilizer fibers, or treated with wet strength agents. Mixtures of various fibers can be used, including coform, which comprises thermoplastic fibers and wood fibers deposited together in an airlaying process.

In one embodiment, the absorbent core comprises a molded, three-dimensional high bulk wet laid cellulosic web, such as an uncreped through-air dried web as taught by F.-J. Chen et al. in commonly owned U.S. patent application, Ser. No. 08/912,906, "Wet Resilient Webs and Disposable Articles Made Therewith," filed Aug. 15, 1997; U.S. Pat. No. 5,429,686, issued to Chiu et al. on Jul. 4, 1995; U.S. Pat. No. 5,399,412, issued to S. J. Sudall and S. A. Engel on Mar. 21, 1995; U.S. Pat. No. 5,672,248, issued to Wendt et al. on Sep. 30, 1997; and U.S. Pat. No. 5,607,551, issued to Farrington et al. on Mar. 4, 1997; all of which are herein incorporated in their entirety by reference.

The "edge width" of the outer shaping member, defined herein as the lateral distance along a continuous portion of the outer shaping member along the transverse centerline, specifically from the inner edge (adjacent the central absorbent member) of the outer shaping member to the outer edge thereof, is desirably at least about 2 mm and specifically at least about 3 mm, more specifically at least about 4 mm. For example, a 7 cm wide rectangular foam section with a 5 cm wide central depression therein for receiving a central absorbent member would have an edge width of 1 cm.

Dimensions of the components of the absorbent article can be suited and optimized for particular functions. For feminine care pads, for example, the outer absorbent member can have a transverse width (distance from one outer longitudinal side to the other across the transverse centerline, not the smaller edge width defined previously) of from about 4 centimeters (cm) to about 8 cm and a length of from about 15 cm to about 30 cm. The central void in the outer absorbent member may have a transverse width of from about 2 cm to about 6 cm, more specifically from about 3 cm to about 5 cm, and can have a length of from about 4 cm to about 18 cm, more specifically from about 6 cm to about 10 cm, resulting in a desirable distance from the longitudinal edge of the central absorbent member to the nearest outer longitudinal edge of the outer absorbent member (which can also be the edge width of the outer absorbent member, assuming no significant gap between the outer absorbent member and the central absorbent member) of from about 0.3 cm to about 2.5 cm, and more specifically from about 0.5 cm to about 2 cm, and more specifically still from about 0.7 cm to, about 1.5 cm. Appropriately larger dimensions would be desirable for diapers and many other absorbent articles. For example, the central absorbent member may be from about 4 cm to about 10 cm in width in a diaper.

Basis weights of the components of the absorbent core can be adjusted and optimized for particular purposes over a wide range. Generally, it is desirable that the basis weight of the central absorbent member be greater than the outer absorbent member because the central absorbent member is intended to contain the primary source of absorbent material for the article, and the outer absorbent member can desirably function as a secondary source of absorbent material when the absorbent capacity of the central absorbent member is exceeded. Thus, the basis weight of the central absorbent member can range, for example, from about 100 grams per square meter (gsm) to about 1000 gsm, more specifically from about 150 gsm to about 600 gsm, and more specifically still from about 200 gsm to about 500 gsm. The basis weight of the outer absorbent member (or, in some embodiments, of the outer shaping member) can range from about 50 gsm to about 2000 gsm, more specifically from about 150 gsm to about 900 gsm, and most specifically from about 200 gsm to about 400 gsm.

As an alternative to an outer absorbent member, an outer shaping member can be used whose primary function is not to absorb fluids but to provide overall shaping, comfort, and integrity. Since a suitably sized central absorbent member can frequently provide the full absorbent capacity needed for typical fluid loadings in many absorbent articles, the outer portions of the absorbent core often need not be absorbent. Thus, serving, for example, either as a ring of material around the central absorbent member or as a pair of longitudinal bands outside the central absorbent member, an outer shaping member helps define the shape of the article, particularly for sanitary napkins when attached adequately to the wearer's panties. In conventional sanitary napkins, the article can become excessively bunched or compressed when wetted, but by maintaining the outer shaping member in a dry state, it can maintain its shaping and body fit functions throughout use. Thus, the outer member in the absorbent core can serve as a shaping and body fit element and optionally as a "cradle" to hold the central absorbent member in place. Thus, the outer member need not be absorbent at all but can be a flexible frame member, though it is preferred that the outer member be absorbent.

The shaping member can be porous, such as a ring of a polyurethane foam; a polyethylene foam such as the product known as VOLARA™ 2a polyethylene foam, obtained from Voltek Corp., of Lawrence, Mass.; or a foam rubber material (e.g., foamed styrene butadiene), foamed silicones, or foamed vinyl plastics. Several such foams can be obtained from Woodbridge Foam Fabricating, Inc., located in Chattanooga, Tenn., from the E. N. Murray Company, Inc., located in Denver, Colo., and Astro-Valcour, Inc., located in Glens Falls, N.Y. Foam materials desirably have a density of about 0.02 grams per cubic centimeter (g/cc) to about 0.1 g/cc. The foam material desirably is treated to be absorbent and/or hydrophilic, but need not be hydrophilic.

The outer shaping member can be a composite element, such as a layer of cellulosic fibers joined to a polymeric foam layer. In one embodiment, the outer shaping member is extensible such that its size can be adjusted for improved fit. The outer shaping member can also be biodegradable and/or flushable, if desired. The outer shaping member can comprise a central hole passing completely through the member to receive the central absorbent member. Principles previously given for the form and properties of the outer absorbent member generally apply to the outer shaping member as well.

Other components may be combined with the cellulosic materials of the absorbent core or added as separate components, layers, or portions of the article. Such other components include odor absorbing components such as baking soda, talc powder, cyclodextrin, ethylenediamine tetra-acetic acid or other chelating agents, zeolites, activated silica, and activated carbon granules, fabrics or fibers; superabsorbent particles and fibers; antimicrobial agents including the silver-loaded zeolites of BF Technologies, located in Beverly, Mass., sold under the trademark HEALTHSHIELD™, as well as triclosan products, chitosan or chitin derivatives; polycarboxylic acids; encapsulated perfumes; emollients such as lanolin; or skin wellness agents such as aloe vera extract, emu oil, avocado oil, grape seed extractives, or vitamin E. Thermoplastic binder fibers may be added, with or without subsequent heat treatment for improved stability. Foam layers, foam shape-defining components, or foam particles may also be present. Plastic inserts to define shape or maintain integrity may also be used.

Additional strategies can further improve the fit, flexibility, comfort, and fluid handling properties of absorbent articles according the present invention. The strategic addition of polymeric webs or wicking barriers in the absorbent core can be especially helpful in the context of the present invention. As used herein, the term "polymeric web" refers to a porous or nonporous layer primarily Composed of polymeric material, and can be a nonwoven web, a plastic film, a polymeric film, an apertured film, or a layer of foam. Polymeric webs can be used as wicking barriers, baffle layers, backsheets, and, if sufficiently liquid pervious, as topsheets of absorbent articles. A polymeric web can consist of about 50 weight percent or more polymeric material, more specifically about 80 weight percent or more polymeric material, and most specifically about 90 weight percent or more polymeric material. Exemplary materials include polyolefins, polyesters, polyvinyl compounds, and polyamides.

In one preferred embodiment, a film or web barrier material is used to separate a central absorbent member from an outer absorbent member in the absorbent core of the article. The film or web can be a transfer delay layer (or a pervious horizontal wicking barrier) intended to slow the vertical capillary transport of fluid from an upper layer of absorbent material to a preferably wider lower layer of absorbent material, or it can be a vertical wicking barrier intended to prevent, impede, or delay lateral wicking from a central absorbent member to a surrounding outer absorbent member. Examples of absorbent articles comprising transfer delay layers between horizontal layers of absorbent material are given in commonly owned U.S. patent application Ser. No. 60/079,657, "An Absorbent System for Personal Care Products Having Controlled Placement of Visco-Elastic Fluids" by A. S. Burnes et al., herein incorporated by reference in its entirety. Examples of absorbent articles comprising a central absorbent member, a wicking barrier, and an outer absorbent member are given in commonly owned U.S. patent application Ser. No. unknown, "Absorbent Article with Center Fill Performance," filed on Oct. 2, 1998, herein incorporated by reference in its entirety.

In the case of a barrier material or transfer delay layer disposed horizontally between two layers of absorbent material, the barrier material desirably is not adhesively attached to both absorbent layers across the full surface of the barrier material, but is unattached over a substantial portion of its area on at least one side such that the two layers of absorbent material in contact with the barrier material can flex apart or become separated by a vertical gap under suitable lateral compression. Desirably, shaping lines such as cut or perforated regions or grooves in the upper layer are suitably placed to promote upward bending of the upper layer and development of a significant gap between the upper layer and the lower layer during lateral compression of the article, particularly when outer crease lines effect a downward folding along or near the crease lines. It is even more desirable if the gap formed between two layers during compression is made directly accessible to fluid flow by providing appropriate slits, cuts, or holes or apertures in the absorbent core that can open up during lateral compression such that fluid can flow into the gap, either after passing through the topsheet or through slits or other openings in the topsheet. The ability to create additional void space in the absorbent article during lateral compression, as occurs when a gap is formed between two layers, is one of several advantages of the present invention over many previous attempts at creating improved body fit in absorbent articles. Thus, in some embodiments, the effect of lateral compression is not only to create an upwardly rising central hump or mound for better body fit, but also to create a void space, desirably surrounded by absorbent material, that can receive fluid, particularly gushes of fluid.

In one preferred embodiment, an upper absorbent layer is separated from a wider lower absorbent layer by a transfer delay layer such as a meltblown or spunbond nonwoven web having a width between that of the upper layer and the lower layer. The longitudinal sides of the upper absorbent layer define crease lines with a sharp transition in material properties (there are two or more layers of absorbent material on the inner side of the crease line, and one less layer of absorbent material on the outer side of the crease line) which promote formation of a valley along the crease line when the absorbent article is compressed laterally in the crotch region.

In the case of a barrier material serving as a barrier to lateral wicking between a central absorbent member and an outer absorbent member, the wicking barrier spans a vertical distance in the absorbent article between the central absorbent member and outer absorbent member. The vertical component prevents or reduces wicking from the central absorbent member toward the longitudinal sides of the article. Further, the vertical component of the wicking barrier divides the absorbent core to serve as a hinge during lateral compression to promote folding, serving as a crease line.

In addition to the vertical component of the wicking barrier, it is also desirable that the wicking barrier further comprise a horizontal component on the surface of the absorbent core forming a ledge to provide further separation of the outer absorbent member from the central absorbent member during use. The vertical component of the wicking barrier can be substantially symmetrically disposed about the longitudinal centerline of the article in the crotch region and serves to promote center filling of the absorbent core and prevent flow of liquid to the longitudinal sides of the article, particularly in the crotch region. The wicking barrier, particularly its longitudinal span in the crotch region, defines a zone of separation between the outer absorbent member and the central absorbent member and naturally serves as a crease line where folding of the article can occur during lateral compression. A shaping line in the central absorbent member, especially a cut, pierced, perforated, pre-folded, or embossed zone, can, if provided with a suitable shape, promote upward bending of the central absorbent member when the article is compressed laterally. The interaction of the creasing line, which tends to result in formation of a valley after lateral compression, with the sharply defined upward folded region of the central absorbent member as promoted by the presence of a shaping line, results in a configuration that offers good body fit and good fluid handling. Fluid that might roll off the central absorbent member can be held and retained in the valley and be absorbed by the absorbent core, particularly by the central absorbent member. Gushes or surges of liquid beyond what can be taken up rapidly by the central absorbent member can be retained by the valley along the crease line for subsequent absorption. Meanwhile, the elevated portion of the central absorbent member, as defined by the shaping lines, can effectively contact the body to result in better intake, less fluid travel along the body toward points of leakage, and reduced smearing of fluid on the cover or topsheet of the article.

The wicking barrier can comprise any barrier material that reduces lateral wicking of fluid from the central absorbent member to the surrounding outer absorbent member.

The barrier spans a finite vertical distance in the absorbent article, such as about 1 mm or greater, specifically about 2 mm or greater, more specifically about 3 mm or greater, and most specifically from about 4 mm to about 15 mm. The barrier material can be a polymeric film or plastic film; a nonwoven web; a layer of rubber, silicone, or other non-absorbent materials; or a less pervious paper sheet including, for example, glassine, wax paper, impregnated papers, paper-polymer composites, densified tissue, tissue containing internal sizing to render it less hydrophilic or tissue treated with hydrophobic matter such as wax, silicone, thermoplastic material, or polyolefins. Flexible hydrophobic foams may also be used, such as a closed-cell polyurethane foam or a silicone foam. A low density hydrophobic web such as a bonded carded web of a polyolefin (such as materials commonly used for surge layers in diapers, but without surfactants or other hydrophilic treatments) can also be used, including the transfer delay barrier materials disclosed in the commonly owned U.S. patent application Ser. No. 60/079,657, "An Absorbent System for Personal Care Products Having Controlled Placement of Visco-Elastic Fluids" by A. S. Burnes et al. Desirably, the barrier material will have a porosity less than 90%, specifically less than 50%, more specifically less than 30%, and more specifically the barrier material will be substantially nonporous or substantially impermeable, though a small number of apertures or small openings can be provided in selected portions of the barrier material to prevent oversaturation of the central absorbent member. With apertures added, it is still desirable that the average open area of the barrier material be less than 20% and more specifically less than about 10%. Suitably, the thickness of the wicking barrier can be about 5 mm or less, specifically about 2 mm or less, more specifically about 1 mm or less, and most specifically about 0.5 mm or less. In some cases, such as when a barrier material in the form of a flexible polymer sheet is used, including a polypropylene or polyethylene web, the barrier material can have a thickness of about 0.2 mm or less, more specifically about 0.1 mm or less, and most specifically about 0.08 mm or less, with an exemplary range of from about 0.02 mm to about 0.3 mm.

The barrier material can also comprise hydrophobic matter that is used to impregnate a portion of the outer absorbent member or a portion of the central absorbent member to reduce lateral wicking. Such hydrophobic matter can include adhesives and particularly hot melt adhesives added to the absorbent article while molten; wax; pastes or emulsions comprising waxes; silicone-based fluids, gels, pastes, or caulk; phenolic resins or other resins which are cured after impregnating the fibrous material of the central absorbent member or outer absorbent member; polyolefins or other plastic or hydrophobic material added as powder, particularly sintered powder, or held in place by adhesives, or by thermal bonding.

The barrier material can be placed along a portion of the perimeter of a central absorbent member to reduce or prevent wicking to the surrounding outer absorbent member. When the wicking barrier is a polymeric film or nonwoven web, it desirably has radial dimensions when set in place slightly greater than the radial dimensions of the central absorbent member such that a strip of the material rests on the surface of the absorbent core to define a visible barrier along at least a portion of the perimeter of the central absorbent member.

The barrier can also comprise material from the backsheet of the absorbent article which is embossed, deformed, pleated, or stretched so as to rise above the conventional plane of the backsheet into the barrier zone between the central absorbent member and the surrounding absorbent material. Backsheet material rising to form an inverted V-shaped barrier between two absorbent members can serve as an effective hinge, if the two adjacent vertical layers in the inverted V are not bonded together. Likewise, the wicking barrier can comprise material from the topsheet that penetrates into the absorbent core to separate the central absorbent member from the outer absorbent member or from an outer shaping member, particularly when the topsheet material is rendered impervious or hydrophobic by chemical treatment, impregnation of adhesive or thermoplastic material, or heat sealing.

The degree of elevation of the central absorbent member can be quantified in terms of a Vertical Deformation test. As used herein, "Vertical Deformation" refers to the height increase experienced by the body-side surface of an absorbent article when the longitudinal sides in the crotch reason are gripped and steadily moved inward toward the longitudinal axis of the article, decreasing the span between the longitudinal sides by 1.5 cm. The Vertical Deformation test apparatus comprises two clamps having a clamp width (longitudinal length of the clamped portion of the edge of the article) of 5 cm. One clamp is stationary and the other is on a track that permits the clamp to slide to increase or decrease the distance between the clamps while keeping the clamp aligned and parallel to the other clamp. The clamps should be tilted downward at an angle of 20 degrees relative to horizontal, such that both outer edges of the absorbent article are slightly elevated relative to the nearest crease line, thus somewhat simulating the positioning of the outward edges of the absorbent article that may be induced by panties with elevated elastic edges in the crotch region. The clamps are 5 cm above the surface of the track, permitting a pad to be suspended in air between the clamps, gripped in the crotch area such that a portion of the longitudinal sides of the absorbent core are held, with the clamps extending inward no more than about 3 mm from the outer edge of the absorbent core. The article should be held substantially taut in the region between the clamps without damaging the article, such that the crotch region is substantially horizontal before lateral compression begins. At a rate of about 0.5 centimeters per second (cm/s), the slidable clamp is moved smoothly toward the fixed clamp. The height of the center of the pad or absorbent article is recorded before the clamp is moved and after the clamp is moved, yielding a difference that is reported as the Vertical Deformation. An increase in height is reported as a positive number, while a decrease is reported as a negative number. Desirably, the Vertical Deformation of the absorbent article is at least about 0.5 cm. Specifically, the Vertical Deformation is at least about 1 cm, and more specifically is at least about 1.5 cm and up to about 10 cm. Desirably, an absorbent article of the present invention exhibits an increase in Vertical Deformation in the crotch region of at least about 20%, and more specifically at least about 50%, relative to the Vertical Deformation in the crotch region exhibited by an essentially identical absorbent article without a shaping line.

As used herein, the term "otherwise essentially identical absorbent article without a shaping line," and other similar terms, are intended to refer to a control absorbent article that is prepared using essentially identical materials and an essentially identical process as compared to an absorbent article of the present invention, except that the control absorbent article does not comprise or is not prepared with a shaping line described herein. As such, the otherwise essentially identical absorbent article without a shaping line and the absorbent article of the present invention will generally have substantially identical basis weights. As a result of not comprising a shaping line, the otherwise essentially identical absorbent article without a shaping line generally will not exhibit the desired upward deformation, folding, or bending properties described herein as compared to an absorbent article of the present invention.

As used herein, "Central Elevation" is defined as the height difference between the center of the central absorbent member along the transverse centerline of the article and the average height of the longitudinal sides of the central absorbent member along the transverse centerline of the article at the end of the Vertical Deformation Test as described above. The Central Elevation for absorbent articles of the present invention can be at least about 0.5 cm, specifically at least about 1 cm, and more specifically at least about 1.2 cm and up to about 10 cm. Desirably, an absorbent article of the present invention exhibits an increase in Central Elevation in the crotch region of at least about 20%, and more specifically at least about 50%, relative to the Central Elevation in the crotch region exhibited by an essentially identical absorbent article without a shaping line.

A measure of the sharpness of an upward longitudinal fold can also be quantified. As used herein, "Compressed Radius of Curvature" refers to the radius of curvature of the absorbent material along the transverse centerline of the absorbent article at the highest point along the transverse centerline after the article has been compressed laterally by 1.5 cm according to the Vertical Deformation test above. The radius of curvature can be estimated by fitting cutouts of known radius of curvature to the sample at the highest point, normally the longitudinal centerline, with the cutout aligned with and over the transverse axis of the article. Desirably, the Compressed Radius of Curvature is no greater than about 1 cm, more specifically no greater than about 0.5 cm, and most specifically no greater than about 0.3 cm. A sharp upward fold at a slit in the absorbent core can render direct measurement very difficult, in which case it can be taken to have a radius of curvature of about the absorbent material that is rising toward the body-side surface of the article during lateral compression. Desirably, the presence of shaping lines results in a decrease in Compressed Radius of Curvature of at least about 20% and specifically at least about 50% relative to an essentially identical absorbent article without a shaping line. Desirably, an absorbent article of the present invention exhibits a decrease in Compressed Radius of Curvature of at least about 20%, and more specifically at least about 50%, relative to the Compressed Radius of Curvature exhibited by an essentially identical absorbent article without a shaping line.

As used herein, the term "flexure-resistant" refers to an element which will support a bending moment, in contrast to an element which will support only axial forces. Likewise, as used herein, "flexure resistance" is a means of expressing the flexibility of a material or article and is measured according to the Circular Bend Procedure described in detail in U.S. Pat. No. 5,624,423, issued Apr. 29, 1997 to Anjur et al., herein incorporated by reference in its entirety. Flexure resistance is actually a measurement of peak bending stiffness modeled after the ASTM D4032-82 Circular Bend Procedure. The Circular Bend Procedure of Anjur et al. is a simultaneous multidirectional deformation of a material in which one face of a specimen becomes concave and the other face becomes convex. The Circular Bend Procedure gives a force value related to flexure-resistance, simultaneously averaging stiffness in all directions. For comfort, the absorbent article desirably has a flexure-resistance of less than or equal to about 1,500 grams, more specifically about 1000 grams or less, more specifically still about 700 grams or less and most specifically about 600 grams or less. For shaping performance, the central absorbent member as well as the outer absorbent member can have a flexure resistance of at least about 30 grams, more specifically at least about 50 grams, and most specifically at least about 150 grams.

As used herein, the term "horizontal," refers to directions in the plane of the article hat are substantially parallel to the body-side surface of the article, or, equivalently, substantially normal to the vertical direction of the article, and comprises the transverse direction and the longitudinal direction of the article, as well as intermediate directions. The orientation of components in an article, unless otherwise specified, is determined as the article lies substantially flat on a horizontal surface.

As used herein, "thickness" of a fluff pad or other absorbent element refers to thickness measured with a platen-based thickness gauge at a load of about 0.05 pounds per square inch (psi) [about 35 kilograms per square meter]. The thickness of the central absorbent member or the outer absorbent member or of the absorbent article in general can be from about 2 mm to about 50 mm, more specifically from about 3 mm to about 25 mm, more specifically still from about 3 mm to about 15 mm, and most specifically from about 4 mm to about 10 mm. Ultrathin articles can have a thickness less than about 6 mm.

As used herein, the "crotch region" of an absorbent article refers to the generally central region that will be in contact with the crotch of a user, near the lowermost part of the torso, and resides between the front and rear portions of the article. Typically the crotch region contains the transverse centerline of the article and generally spans approximately 7 to 10 cm in the longitudinal direction.

Referring to FIG. 1, a top view of a sanitary napkin 10 is depicted. The napkin 10 has a topsheet (not shown), a backsheet 26 connected to wings 28, and further comprises an absorbent core 12 having a general hourglass shape and having a crotch region 13. The absorbent core comprises a large central absorbent member 14 and a smaller outer absorbent member 16 which comprises two crescent-shaped zones transversely surrounding the central absorbent member 14 in the crotch region 13. Along a major portion of the boundary between either zones of the outer absorbent member 16 and the central absorbent member 14 is a crease line 18, which can be formed by any of the methods known for producing side channels in sanitary napkins and can be an embossed, highly densified region stabilized by infusion or impregnation of thermoplastic material or stabilized by binders in the absorbent material. The crease lines 18 can also comprise slits or other structures that permit the outer absorbent member 16 to fold relative to the central absorbent member 14, particularly such that during lateral compression when in use, the longitudinal sides of the outer absorbent member 16 can fold upward, resulting in a valley (downward folding of the absorbent core) along the crease lines 18, particularly when the central absorbent member 14 folds upward (like an inverted V or U) in the crotch region 13.

The two separated zones of the outer absorbent member 16 may comprise coform, fluff pulp, densified fluff pulp, a densified airlaid web, or other absorbent materials known in the art. The central absorbent member 14 can likewise comprise any known absorbent material, including fluff, mixtures of cellulosic fluff and superabsorbent particles, coform, layers of tissue, air laid webs, cotton, other natural fibers, rayon, and peat moss. Substantially within the central absorbent member 14 is shaping line 20 which influences the deformation of the central absorbent member 14 during lateral compression of the article 10, particularly when compressed laterally along the longitudinal sides of the central absorbent member 14 in the crotch region 13. The shaping line 20 comprises a central longitudinal line 22 having longitudinal endpoints. From each endpoint thereof, a pair of symmetrical outward spanning lines 24 extend from the vicinity of the longitudinal centerline outward toward the longitudinal sides of the central absorbent member 14 and toward the transverse ends of the central absorbent member 14. Desirably, the shaping line 20 comprises slits.

Under the influence of lateral compression in the crotch region 13, the longitudinal sides of the two zones of the outer absorbent member 16 bend upward as the absorbent core 12 along the crease lines 18 bends downward. Meanwhile, the central absorbent member 14 in the crotch region 13 begins to deflect in an inverted V shape, with the cusp of the inverted V being defined by the central longitudinal line 22.

Figure 2:
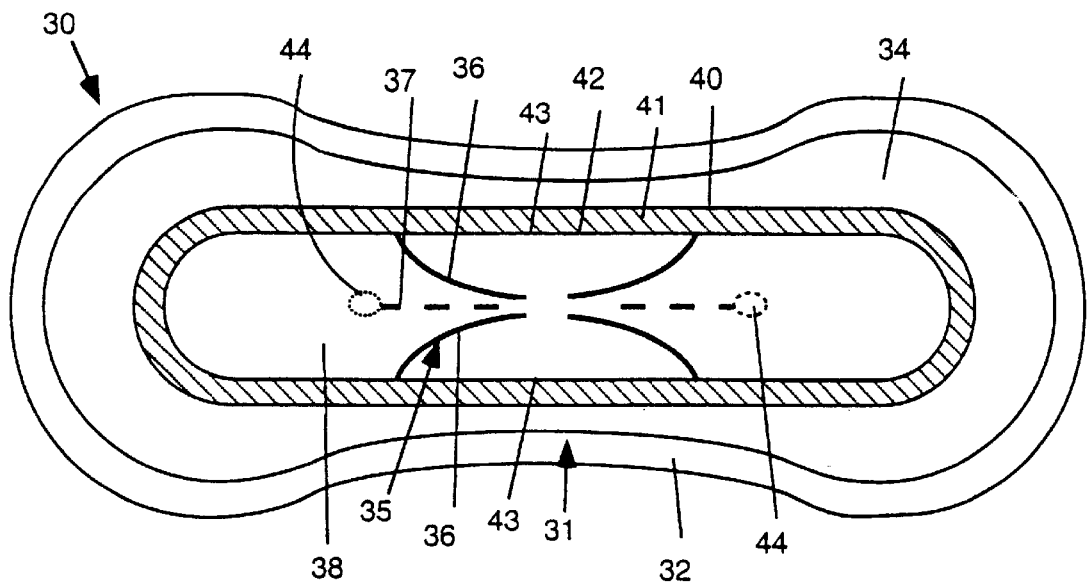
FIG. 2 is a top view of a sanitary napkin comprising linear crease lines along a wicking barrier, arcuate shaping lines in a central absorbent member and attachment points outside the crotch region connecting the central absorbent member to the backsheet for improved body fit and flow handling.

FIG. 2 depicts a top view of a sanitary napkin 30 according to the present invention which comprises a wicking barrier 40 separating a central absorbent member 38 from an outer absorbent member 34. A topsheet (removed to reveal the view of FIG. 2) is connected to the backsheet 32. The central absorbent member 38 is elliptical and is surrounded by the wicking barrier 40 and the outer absorbent member 34, wherein the wicking barrier comprises a vertical component (not visible from the present perspective) that penetrates into the absorbent core to separate the outer absorbent member 34 from the central absorbent member 38, and further comprises a horizontal component 41 extending along the body side surface of the outer absorbent member 34. This configuration reduces leakage and promotes excellent center fill of the article 30, which can be a sanitary napkin, an incontinence pad, or other absorbent article.

The outer absorbent member 34 comprises a central depression or void (not shown) which receives the central absorbent member 38. The inner edge 42 of the wicking barrier 40 marks the location of an interface between the sides of the central absorbent member 38 and the central void or depression (not shown) of the outer absorbent member 34. The interface in the crotch region 31 of the article 30, where the vertical component of the wicking barrier 40 is present, serves as a crease line 43 during lateral compression of the article in the crotch region 31. Since the outer absorbent member 34 and central absorbent member 38 are physically separated and have a low-friction wicking barrier 40 between them, the bending stiffness along the crease line 43 is low and downward bending there to form a valley is greatly facilitated.

The central absorbent member 38 comprises shaping line 35 comprising outwardly concave arcs 36 and a central longitudinal line 37, which may be a series of perforations, notches, cuts, tears, or slits having portions not fully perforated, notched, cut, torn, or slit along its length for increased integrity. Likewise, the arcs can be, for example, slits but desirably should not completely sever a portion of the central absorbent member 38. When the article 30 is laterally compressed, the arcs define bending lines which permit the central portion of the central absorbent member 38 to rise sharply upward, with the portions of absorbent material contained within the outwardly concave arcs rising steeply from the valleys defined along the crease lines 43. The curvature of the central absorbent member 38 along the longitudinal centerline of the article (the longitudinal axis passing through the center of the article in the plane thereof, which in this case includes the central longitudinal line 37) can be beneficially controlled by forming attachment regions 44 on the central absorbent member 38, where the central absorbent member 38 is connected adhesively (achievable by chemical adhesives, ultrasonic bonding, thermal bonding, etc.) or mechanically (e.g., by sewing, or by fiber entanglement from needling or embossing) to the backsheet 32 to prevent significant upward deflection in that region and to encourage upward curl of the transverse ends of the article with respect to the longitudinal centerline. The attachment regions 44 are located substantially on or near the longitudinal centerline of the article 30 and are located roughly outside the crotch region 31 or near the longitudinal boundaries of the crotch region 31, away from the transverse centerline (the axis normal to the longitudinal centerline, at the longitudinal midpoint of the article, in the plane thereof and the region of maximum elevation induced by the shaping line 35. Thus, when the article 30 is compressed laterally, the article can more easily assume an upwardly curved shape along the longitudinal centerline and a W-fold shape in the crotch region 31, substantially without a W-fold shape outside the crotch region 31, due to the combined influence of the crease lines 43, the shaping line 35, and the attachment regions 44.

Figure 3:
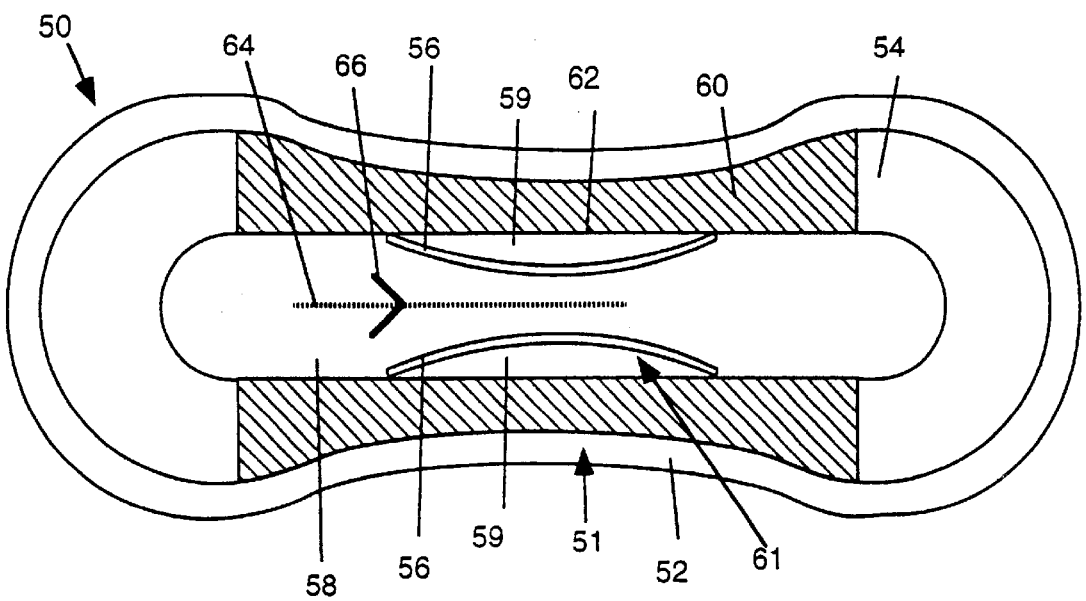
FIG. 3 is a depiction of another embodiment of a sanitary napkin comprising crease lines, shaping lines, and a wicking barrier with an extensive horizontal component.

FIG. 3 depicts a top view of an absorbent article 50 comprising a backsheet 52, a topsheet (not shown), an outer absorbent member 54 having a central void (not shown) for receiving a central absorbent member 58 having shaping lines 61 therein, and a wicking barrier 60 between a portion of the longitudinal sides of the central absorbent member 58 and the outer absorbent member 54. The article 50 is similar in construction to the article 30 of FIG. 2, but the wicking barrier 60 does not completely surround the central absorbent member 58 but provides separation between the central absorbent member 58 and the surrounding outer absorbent member 54 in the crotch region 51 and somewhat beyond the longitudinal extent of the crotch region 51. As such, the crease line is effectively identical to the longitudinal sides 62 of the central absorbent member 58. In further contrast to FIG. 2, in FIG. 3 the wicking barrier 60 extends from the longitudinal sides 62 of the central absorbent member 58 to the longitudinal sides of the outer absorbent member 54 along the surface of the outer absorbent member 54, which can reduce wicking contact of the central absorbent member 58 with the outer absorbent member 54 during use when the article 50 is bunched or compressed, thus reducing leakage from the sides.

The shaping line 61 comprises a pair of outwardly concave arcuate lines 56, which may be embossed or formed by other known densifying methods, or may be cut or slit or perforated preferably without complete severance of the crescent-shaped zones 59 between the arcuate lines 56. The shaping line 61 further comprises a central longitudinal line 64 and a pair of outward spanning lines 66 to assist in the shaping of the central absorbent member 58 during use.

Figure 4:
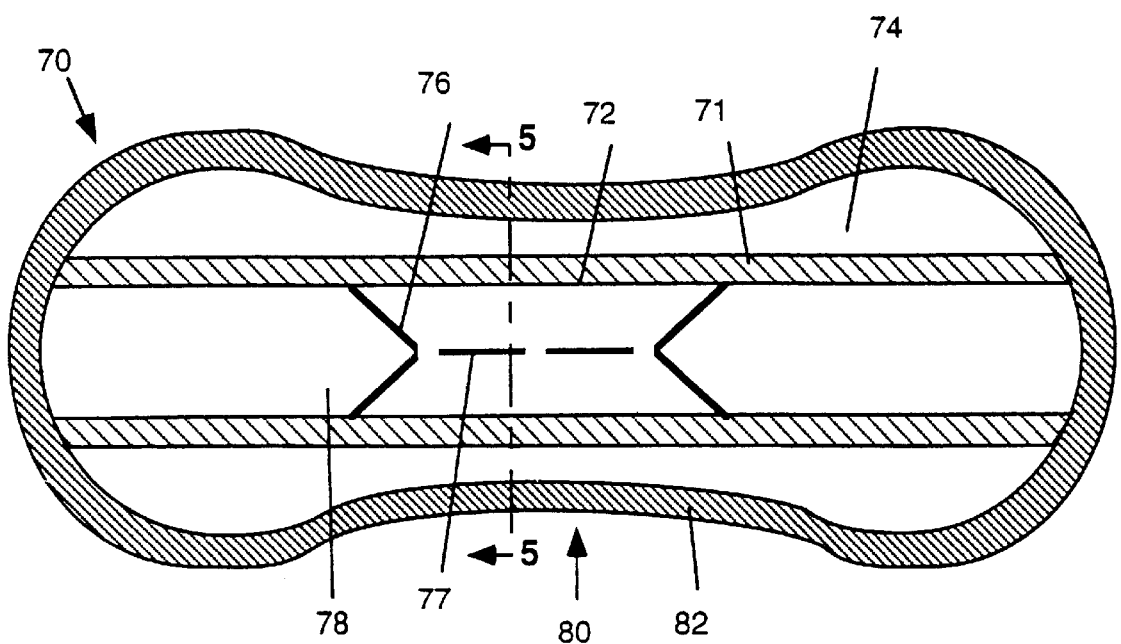
FIG. 4 is a top view of a sanitary napkin comprising a vertical wicking barrier with a horizontal component extending longitudinally across the article, further comprising shaping lines in the central portion of the article.

FIG. 4 depicts the top view of a sanitary napkin 70 according to the present invention comprising a topsheet (not shown), a backsheet 82, an outer absorbent member 74 split longitudinally into two zones, a central absorbent member 78 between the two zones of the outer absorbent member 74, a wicking barrier 71 having a vertical component (not shown) along the outer edge 72 of the central absorbent member 78, separating the vertical walls of the outer absorbent member 74 from the central absorbent member 78, the wicking barrier 71 further comprising a horizontal component (visible as the exposed portion of the wicking barrier 71) on the surface of the outer absorbent member 74. The crease line is effectively identical to the location of the vertical component of the wicking barrier 71 along the outer longitudinal edge 72 of the central absorbent member 78. The central absorbent member 78 comprises a shaping line comprising two sets of outward spanning lines 76 at the longitudinal ends of a central longitudinal line 77, which, as drawn comprises two short sections. The outward spanning lines 76 preferably comprise slits, perforations, or other stiffness reducing means. When compressed laterally in the crotch region, the article 70 should deform to form valleys along the crease lines 72 in the crotch region 80 and form an elevated central region in the central absorbent member 78.

Figure 5:
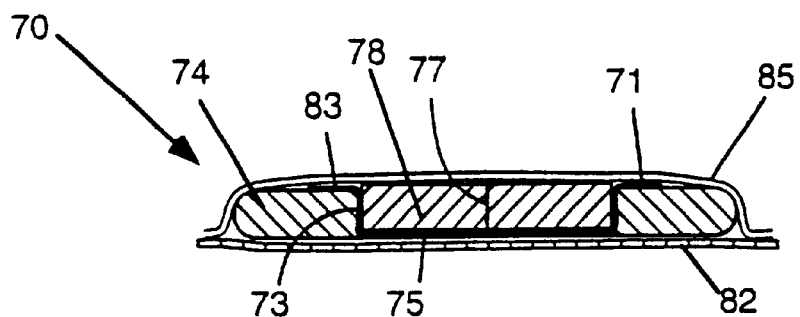
FIG. 5 is a sectional view of the article in FIG. 4 depicting the components of the wicking barrier.
Figure 6:
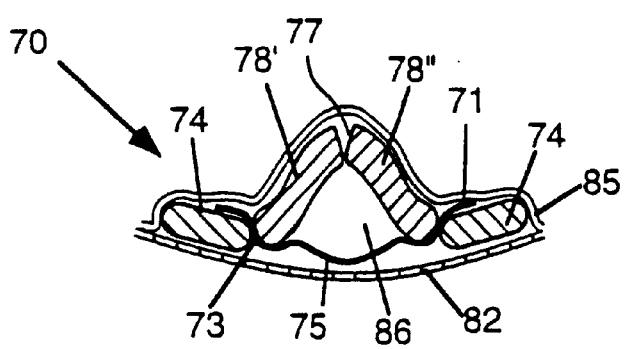
FIG. 6 shows how the cross-section of FIG. 5 may appear after the article has experienced lateral compression.

FIG. 5 depicts a cross section of the absorbent article 70 of FIG. 4, with the topsheet 85 now shown. The wicking barrier 71 comprises a horizontal component (now labeled as 83), a vertical component 73, and an underlying portion 75 beneath the central absorbent member 78. The longitudinal central shaping line 77 is depicted here as a slit that extends through the thickness of the central absorbent member 78, though it could be made to extend a smaller distance into the central absorbent member 78. When laterally compressed, the article 70 shown in FIG. 5 can be deformed as shown in FIG. 6. The underlying portion 75 of the wicking barrier 71 is not adhesively attached to the central absorbent member 78, permitting it to deflect upward independent of the downward deflection of the outer absorbent member 74 and the backsheet 82. The independent deflection of the outer absorbent member 74 and the central absorbent member 78 (shown as having a first side 78' and second side 78") permits creation of additional void space in the article 70, and particularly the formation of a chamber or void 86 beneath the central absorbent member 78. This void can help retain additional fluid.

Figure 7A:
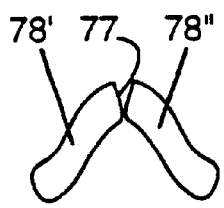
FIG. 7 shows a deformed central absorbent members from FIG. 6 with various alternate shaping lines.
Figure 7B:
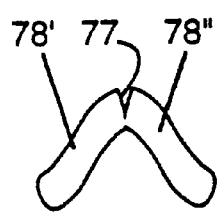
Figure 7C:
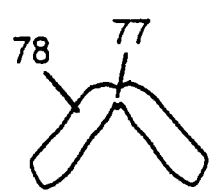

FIG. 7 shows alternative forms that the central absorbent member 78 may take in lateral compression, as shown in FIG. 6, depending on the nature of the longitudinal central shaping line 77. FIG. 7A depicts the case when the longitudinal shaping line 77 is a slit, permitting slight separation of the first portion 78' from the second portion 78" in the central absorbent member 78. In FIG. 7B, the longitudinal shaping line 77 is a notch. In FIG. 7C, the longitudinal shaping line 77 is a densified region. Differences in the nature of the shaping line can affect the Vertical Deformation of the central absorbent member 78, the radius of curvature of that element, and other properties of the absorbent article.

Figure 8A:
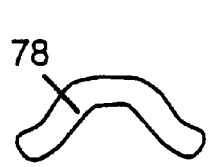
FIG. 8 shows deformations of the central absorbent member of the article from FIG. 4 along other transverse sections away from the transverse centerline of the article.
Figure 8B:
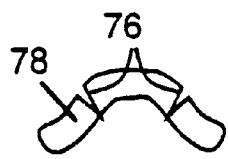

FIG. 8 shows the transverse cross-sectional shapes of the central absorbent member 78 away from the transverse centerline of an absorbent article under lateral compression. In FIG. 8A, the shape of the central absorbent member 78 just outside the region of the shaping lines is shown where the article may undergo a transition from a central inverted-V shape or inverted-U shape in the crotch region to a flatter shape outside the crotch region. In FIG. 8B, the presence of outwardly spanning lines 76 in the form of slits or deep notches are shown.

Figure 9:
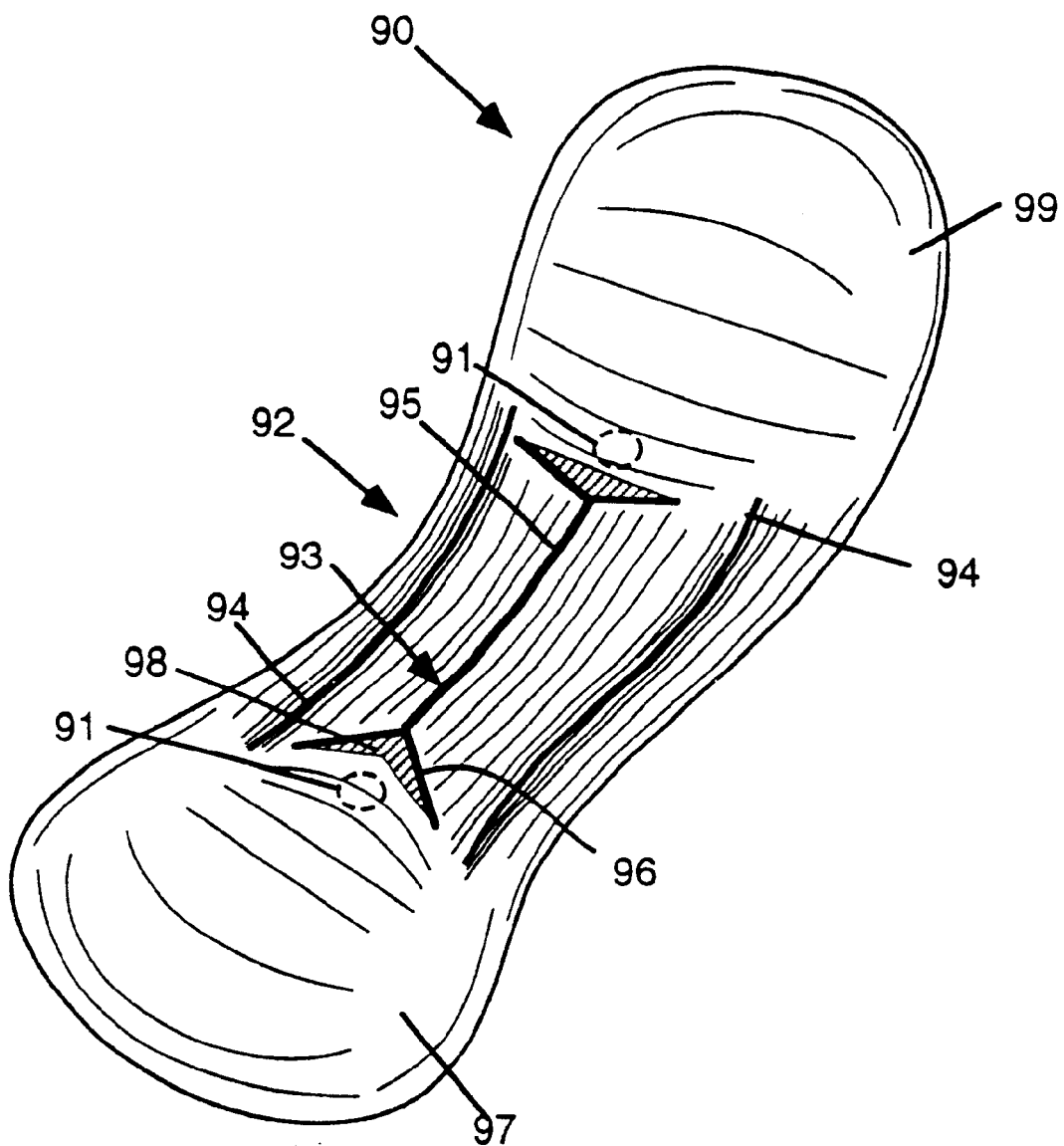
FIG. 9 shows the general shape of an article of the present invention when deformed laterally.

FIG. 9 shows the topography of a sanitary napkin 90 similar to the article 70 of FIG. 4, but under lateral compression in the crotch region 92. Internal structural components such as the wicking barrier or outer absorbent member or central absorbent member are not shown separately to emphasize the topography of the upper surface of the article 90. The crease lines 94 and the shaping line 93 are shown. The shaping line 93 comprises a longitudinal line 95 such as a slit or notch or groove and symmetric pairs of outwardly spanning lines 96 which comprise slits. In the crotch region 92, a W-fold geometry is achieved as a valley is formed about the crease lines 94 and an inverted-V shape is induced by the shaping line 93, which includes a longitudinal component 95 and outward oblique components 96. The oblique components 96 are slits, which permit formation of a gap 98 under the inverted V-shaped region. The slits also partially disengage the crotch region 92 from the front region 97 and the back region 99 so that they can deform somewhat independently of the deformation in the crotch region and so that the front region 97 and the back region 99 have a degree of upward curl along the longitudinal centerline for better conformability. Optionally, the longitudinal curl outside the crotch region 92 can be further enhanced by attaching a portion of the upper layer of absorbent material in the vicinity of the attachment points 91 to the backsheet by embossing, adhesives, ultrasonic bonding, or other means. The attachment points 91 in the front region 97 or back region 99 are desirably near but not within the inverted V-shaped elevated region, and, under lateral compression, can interact with forces transmitted along the outer portions of the absorbent material to deflect the ends of the article upward.

As with other embodiments of the present invention, the presence of the shaping lines (and the optional attachment points 91 in conjunction with shaping line 93) in the central region of the pad permits improved body fit relative to an identical pad without the shaping lines (or, in alternative approaches, relative to an identical pad without the oblique components of the shaping lines or relative to an identical pad without the components of the shaping lines that are off the longitudinal centerline). The presence of the shaping lines 93 during lateral compression result in an inverted U-shape or inverted V-shape in the crotch region while permitting regions outside the crotch region to deform somewhat independently, and permits the crotch region to have a more distinct, more elevated, or more stable shape. For example, comparing the topography of two absorbent articles under lateral compression that are essentially identical except for the presence of a shaping line according to the present invention, the effect of the shaping line can be an increase in Vertical Deformation in the crotch region of at least about 20%, specifically at least about 35%, more specifically at least about 60%, and up to about 500%, relative to an otherwise essentially identical absorbent article without a shaping line.

The increase in Vertical Deformation can be at least about 2 mm, more specifically at least about 5 mm, and up to about 50 mm. The presence of shaping lines can also effectively reduce the Compressed Radius of Curvature along the transverse centerline at the highest portion of the central upward mound by at least about 20%, more specifically by at least about 50%, and up to about 500%, relative to an otherwise essentially identical absorbent article without a shaping line. Further, the maximum elevation rise along transverse profiles of the pad's surface longitudinally away from the ends of the shaping lines (such as a transverse profile line normal to the longitudinal centerline passing over the locations indicated for attachment points 91) can be reduced substantially by the presence of shaping lines 93 or by the presence of outwardly spanning lines 96 in the shaping lines 93. In other words, the shaping lines 93 modify the shape of the crotch region 92 for improved body fit without necessarily causing other regions to deform in the same way, thus permitting, for example, the achievement of a relatively flat front portion of a pad that conforms well to the frontal pudendal region, while also achieving a W-fold in the crotch region. In some embodiments, an inverted V-shape that extends from the crotch region to the back region, for engagement with the buttocks, is desirable, so outwardly spanning lines toward the rear of the crotch region 92 may be removed from the design, along with the rear attachment point 91, but with the shaping line optionally further extended to the desired length.

EXAMPLES

Several examples of absorbent articles were made with the materials listed in Table 1 below:

Table 1. Basic materials used in construction of absorbent articles for the Examples.

| Component | Manufacturer | Description |
| --- | --- | --- |
| Topsheet Spunbond material | Kimberly-Clark Corp. | 0.6 osy polypropylene spunbond web, "Delta" version, treated with 0.3% add-on of surfactant (described below) |

-continued

| Component | Manufacturer | Description |
|---|---|---|
| Surfactant treatment | ICI Americas, Inc. | 45% (w) polyethoxlated hydrogenated ethoxylated castor oil; 55% (w) sorbitan monooleate |
| Adhesive | National Starch and Chemical Co. | NS-34-5610: slot-coated, pinstripe pattern, applied at a level of about 5 gsm or less |
| Fluff | Kimberly-Clark Corp. | Coosa River CR56 debonded softwood pulp comminuted with a hammermill |
| Densified airlaid webs | | |
| Completed web | Concert Fabrication, Ltee | 90% softwood fibers and 10% binder fibers with overall densities of 0.1-0.2 g/cc. |
| Fibers | Weyerhaeuser Co. | NB-416: bleached southern softwood kraft |
| Binder fibers | Hoechst Celanese Corp (Trevira Company) | Celbond #255 PET core, activated co-polyethylene sheath, 50/50 core/sheath ratio, concentric, 2.8 dpf, with T-255 fiber finish |
| Impervious wicking barrier | | |
| Polyolefin film, colored | Edison Plastics Co. | A low density polyethylene, 20 gsm, rose color, 1 mil initially, 2 mil gauge after embossed with pattern MFST (male fine square taffeta), contact adhesive on one side |
| Polyolefin film, white | | Low density polyethylene, 18 gsm, opaque with added white pigment, about 1 mil |
| Pervious wicking barrier | | |
| Spunbond web | Kimberly-Clark Corp | 0.8 osy 2.7 denier, rose color, no surfactant |
| Backsheet | | |
| Polyolefin film | Edison Plastics Co. | A low density polyethylene, 20 gsm, rose color 2 mil gauge after embossed with pattern MFST (male fine square taffeta), coated with contact adhesive on one side |
| Adhesive | National Starch and Chemical Co. | NS-34-5610, less than 15 gsm added, slot-coated, pinstripe pattern |
| Garment adhesive | National Starch and Chemical Co | NS-34-5602, less than 45 gsm applied, slot coated, two 15 mm side lines of adhesive with a 19 mm space between them |
| Release paper | Akrosil Inc. | White base sheet, one side coated with silicone release agent, other side printed |

Figure 10:
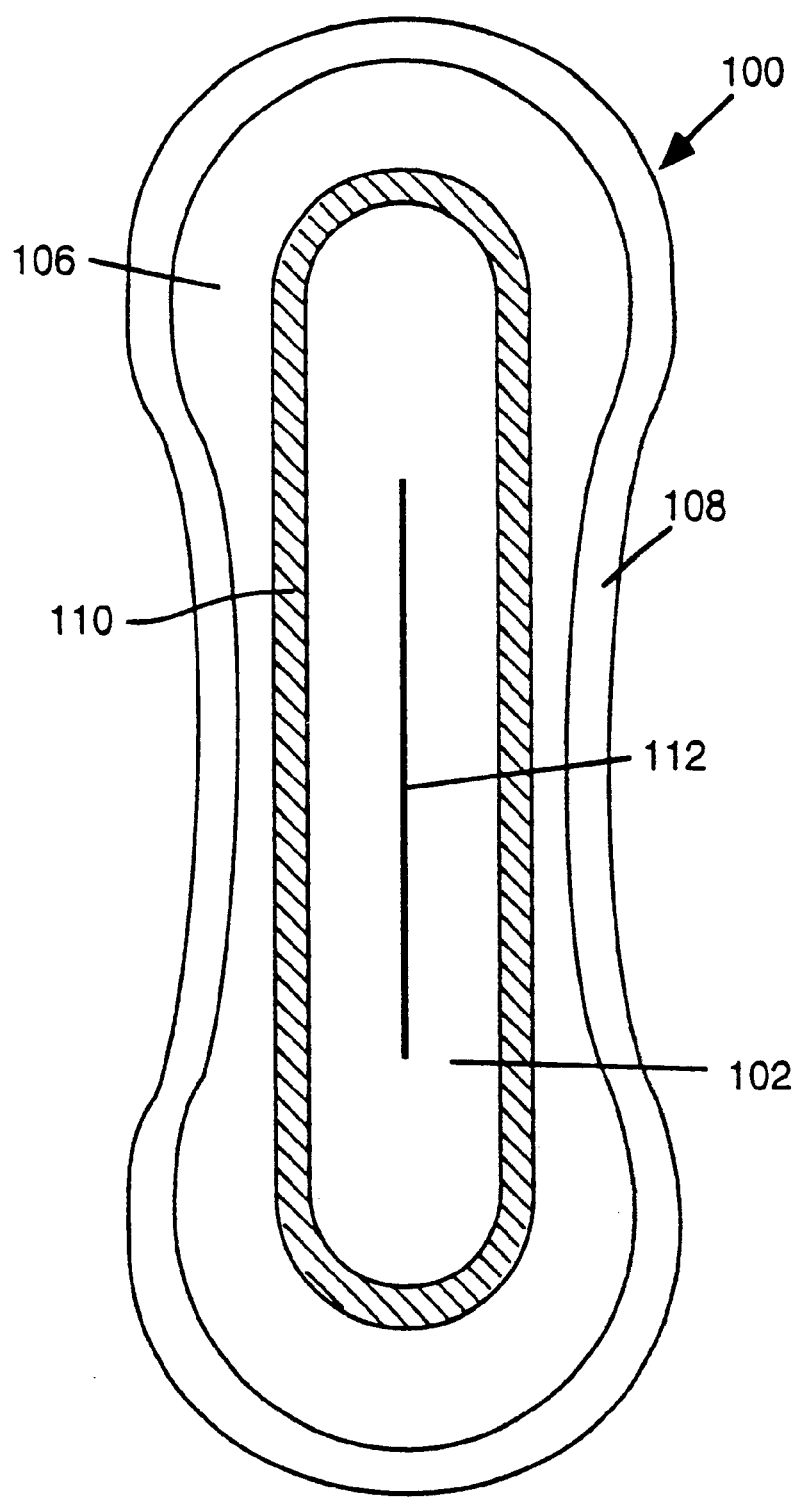
FIG. 10 shows a pad comprising a central absorbent member, a wicking barrier, and an outer absorbent member with a longitudinal slit in the central absorbent member.

Example 1 and other examples described herein were made to have a top view appearance according to FIG. 10, prior to the addition of outwardly spanning lines in the central absorbent member. FIG. 10 depicts an article 100 having a central absorbent member 102 surrounded by a hydrophobic ledge 110 (the horizontal component of a wicking barrier) and a larger absorbent member 106, which may be an outer absorbent member having a central void or depression or an underlying absorbent member without a central void or depression. The absorbent core comprising the central absorbent member 102 and the outer or underlying absorbent member 106 are enclosed by an underlying backsheet 108, with larger dimensions than the absorbent core to form a rim therearound, and a topsheet (not shown) which is attached to the backsheet 108 at the rim.

Example 1 was a pad made without a vertical wicking barrier but with a horizontal wicking barrier; i.e., with a polymeric film disposed horizontally between two superposed absorbent layers. Thus, in Example 1, the horizontal ledge 110 is the exposed horizontal component of a purely horizontal wicking barrier (the impervious wicking barrier of Table 1) which lies in a plane between an upper central absorbent member 102 and an underlying outer absorbent member 106, which is merely a planar absorbent member which lies beneath the central absorbent member 102 (in several other examples according to the present invention, the outer absorbent member has a central void into which the central absorbent member is inserted).

In Example 1, a 175 gsm densified airlaid web (as described in Table 1) served as the lower layer of the absorbent core, i.e., as the outer absorbent member 106 without a central void or depression. The 175 gsm airlaid outer absorbent member was cut to a dumbbell shape with a length of about 21.5 cm and a width at the transverse centerline of about 6 cm. The dumbbell-shaped outer absorbent member was placed on the backsheet 108 (as described in Table 1) comprising a polymer film provided with contact adhesive. Over the central portion of the outer absorbent member 106 was placed a cut rounded rectangular section of spunbond film (the same material as the pervious wicking barrier of Table 1) to serve as a horizontal wicking barrier or a transfer delay barrier, the outer edge being visible as the horizontal ledge 110. The horizontal wicking barrier had a length of 20.3 cm and a width of 4.7 cm. Above the horizontal wicking barrier was placed a rectangular rounded central strip of a densified airlaid web having dimensions smaller than the cut spunbond film (18.7 cm long and 3.7 cm wide) serving as an upper layer or central absorbent member 102 in the pad. The densified airlaid strip was as described in Table 1, with a density of about 0.1 g/cc and a basis weight of about 175 gsm. A slit 112 about 10 cm long was provided through the longitudinal center of the central strip in the longitudinal axis. The spunbond topsheet as described in Table 1 was then placed over the entire article, with edges extending well beyond the outer absorbent member 106. The laminated structure was then cut with a dumbbell-shaped die having dimensions greater than the outer absorbent member (24.4 cm long, 8 cm wide at the transverse centerline) to provide a rim of backsheet material 108 and cover material (not shown) around the outer absorbent member 106 in an absorbent article 100 having good integrity provided in part by the contact adhesive on the polymeric film.

Under lateral compression, the pad 100 shows some upward deflection in the central absorbent member 102, but the deflection extends throughout much of the pad.

Figure 11:
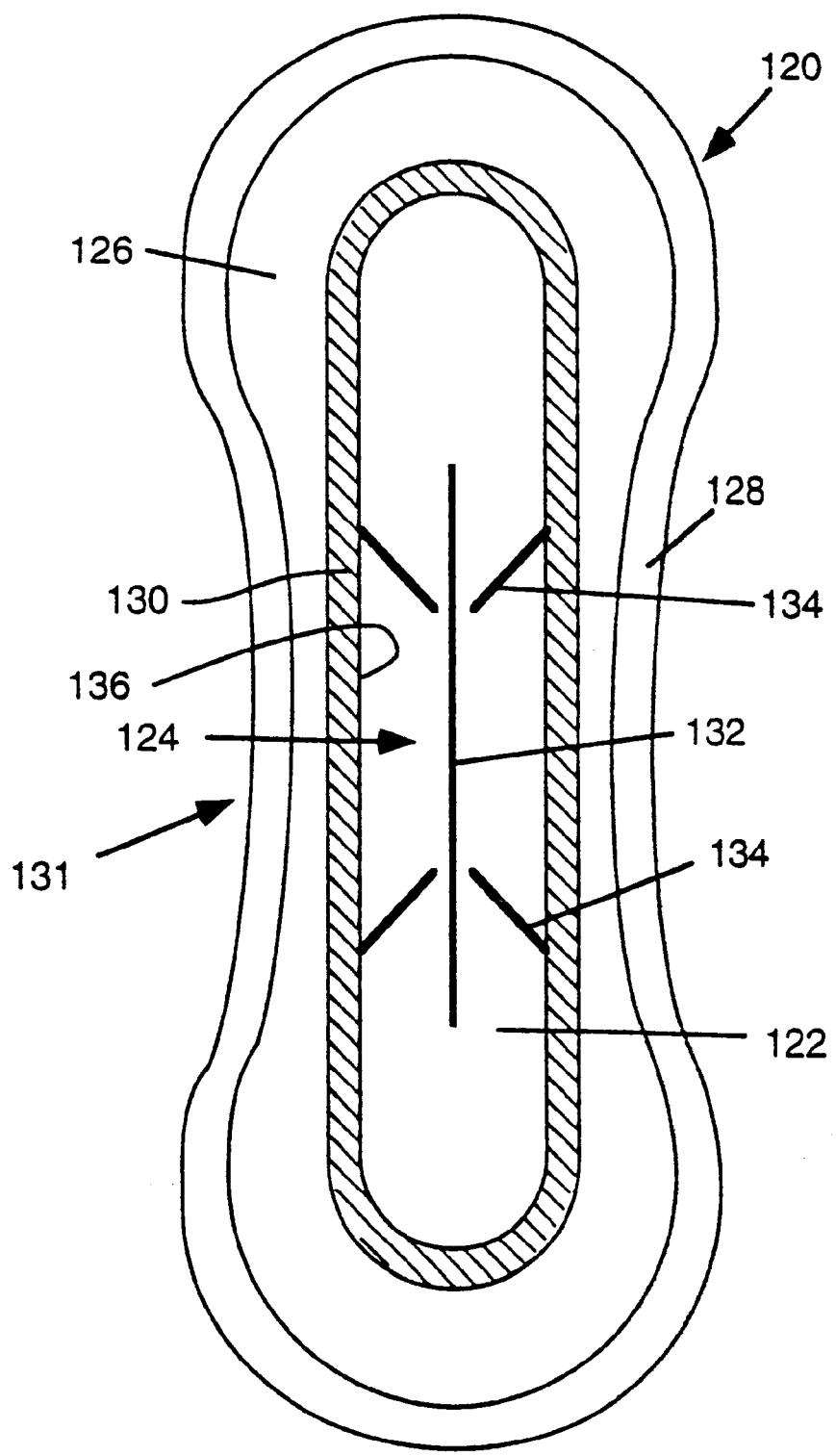
FIG. 11 shows the pad of FIG. 10 further comprising outwardly spanning lines in the central absorbent member.

Example 2 was substantially identical to Example 1 except that outwardly spanning lines in the form of oblique slits were added to the central absorbent member. The slits were made by using scissors to cut slits from the longitudinal sides of the central absorbent member toward the longitudinal centerline, but traversing only about 80% of the distance to the longitudinal centerline to prevent severing a portion of the central absorbent member from the rest of the member. The configuration achieved is depicted in FIG. 11, which shows a sanitary napkin 120 similar to that of FIG. 10 except that the central absorbent member 122 now comprises shaping lines 124 suitable for achieving good body fit in the crotch region 131. As before, the article 120 comprises a central absorbent member 122, the surrounding outer absorbent member 126, a backsheet 128, a horizontal ledge 130 from a wicking barrier, and a topsheet (not shown), using materials described in Example 1. The crease lines correspond approximately to the longitudinal sides 136 of the central absorbent member 122 in the crotch region 131. The shaping line 124 comprises a longitudinal central line 132 and pairs of outwardly spanning lines 134 that work in conjunction with the crease lines 136 to substantially confine the W-shape folding of the article to the crotch region 131 during lateral compression.

For Example 3, feminine pads according to the present invention were made generally following the procedures above for Example 1, with the exceptions that 1) a central region of the outer absorbent member was removed by a die cutting operation to provide a central void in the outer absorbent member having substantially the same dimensions as the central absorbent member (about 18.7 cm long and 3.7 cm wide); 2) a cut polymer film (the rose-colored impervious wicking barrier of Table 1) die cut to be a rounded rectangle 20.3 cm long by 4.7 cm in width was placed over the central void, replacing the similarly shaped spunbond web of Example 1, thus serving as a barrier material for a wicking barrier; 3) an absorbent insert having a shape and dimensions essentially the same as the central void was placed over the cut polymer film to define a central absorbent member in the void surrounded by the remaining portions of the outer absorbent member; 4) the longitudinal slit was not added, but 5) the densified airlaid web serving as the upper layer in the central absorbent member was provided with cuts to serve as shaping lines in the crotch region spanning a major portion of the transverse distance between the longitudinal centerline of the central absorbent member and the longitudinal sides thereof.

In Example 3, the central absorbent member comprised an upper layer consisting of a 250-gsm densified airlaid mat (as described in Table 1) having a density of 0.14 g/cc and a lower layer consisting of the cut-out portion from the 175-gsm airlaid material of the outer absorbent member having a density of about 0.1 g/cc which was previously removed to provide a central void.

Figure 12:
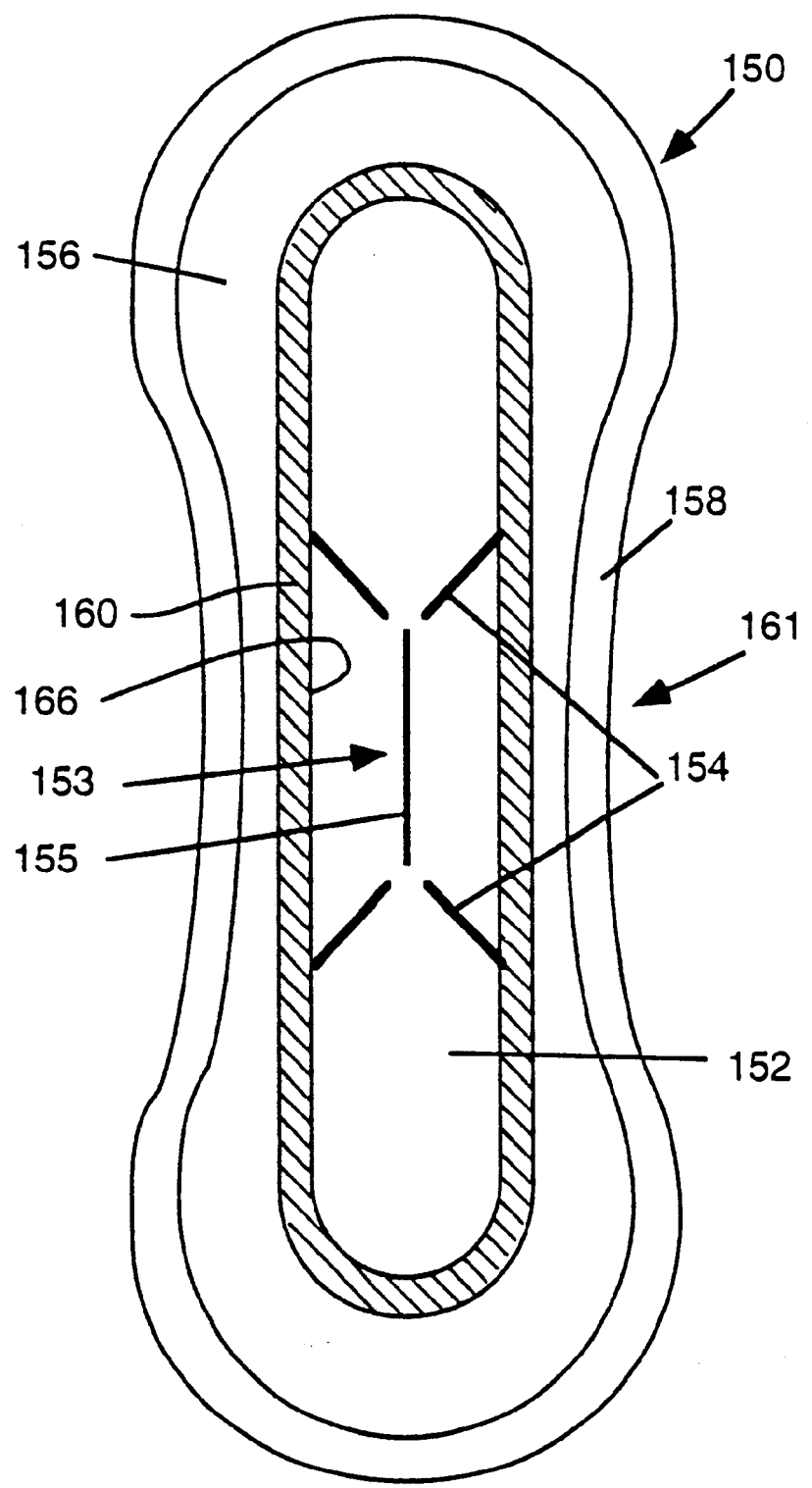
FIG. 12 depicts an article similar to that of FIG. 11, but wherein the outer absorbent member comprises a central void lined with the wicking barrier and further filled with the central absorbent member, wherein the central absorbent member comprises shaping lines.

The geometry of the shaping lines for Example 3 is shown in FIG. 12, where the article 150 comprises a multilayered central absorbent member 152 placed in a void (not shown) within a surrounding outer absorbent member 156, wherein a wicking barrier 160 lines the central absorbent member 152 and also provides a horizontal ledge visible on the surface of the outer absorbent member 156 for good fluid isolation of the two absorbent members 152, 156. The absorbent members 152, 156 reside on a backsheet 158 which is adhesively attached to a spunbond topsheet (not shown). The shaping lines 153 comprise a longitudinal slit 155 and the pairs of outwardly spanning lines 154, which do not traverse the entire distance from the longitudinal centerline to the longitudinal sides 166 of the central absorbent member 152.

After the topsheet was attached and the entire article 150 was die cut to provide a sealed article 150 having a rim of backsheet 158 and topsheet material surrounding the outer absorbent member 156, a ring of the colored barrier material 160 was visible through the translucent topsheet (the horizontal component of a vertical wicking barrier).

The longitudinal sides 166 of the central absorbent member 152 served as crease lines in the crotch region 161. The definition of the elevated region in lateral compression was excellent, being more clearly confined to the crotch region and more definitely shaped than without the shaping lines.

Figure 13:
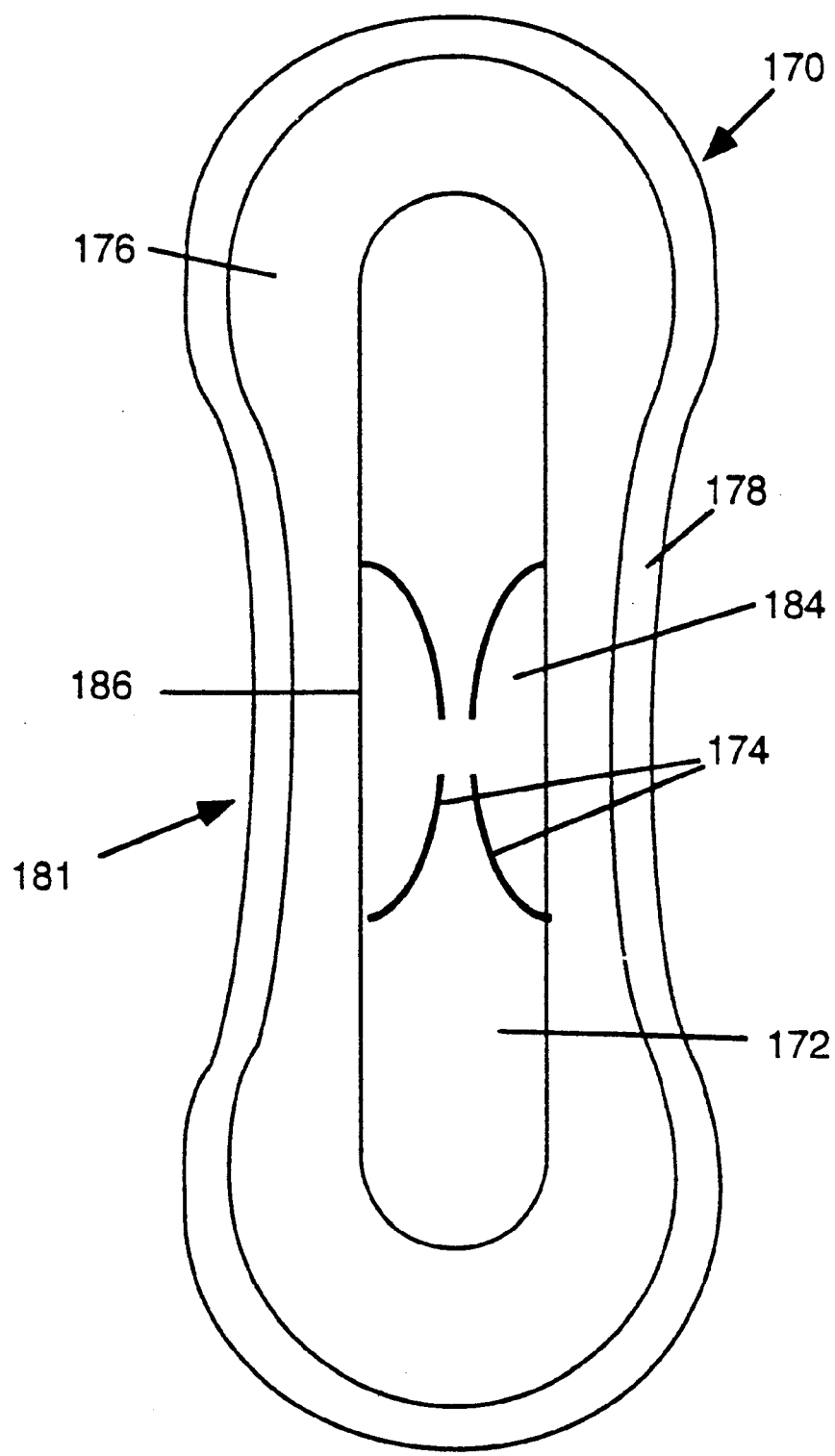
FIG. 13 is a top view of an article without a polymeric wicking barrier comprising an outer absorbent member having a central void therein for receiving a two-layered central absorbent member comprising shaping lines in the upper layer thereof.

Example 4 was produced substantially in the same manner as Example 3, except that no wicking barrier was used and the shaping lines were cut in the upper layer of the central absorbent member in arcuate forms, as shown in FIG. 13. The sanitary napkin 170 comprises an outer absorbent member 176 surrounding a two-layered central absorbent member 172 having arcuate shaping lines 174 in the form of outwardly concave half-ovals, with portions near the centerline not fully severed to maintain strength. The shaping lines 174 nearly circumscribe half-oval shaped regions 184 between the shaping lines and the longitudinal sides 186 of the central absorbent member 172, which also serve in part as crease lines in the crotch region 181. The absorbent core comprising the outer absorbent member 176 and central absorbent member 172 reside between a backsheet 178 and a topsheet (not shown).

The shaping lines 174 largely circumscribed semi-ovals 184 which could rise substantially during lateral compression to provide a slightly flattened inverted V-shape in the crotch region while the crease lines folded downward to provide valleys. In this embodiment, the upper layer of the central absorbent member deflected upward with the upper layer during lateral compression, while the backsheet deflected downwards with the outer absorbent member. A clear W-fold geometry was established in the crotch region 181 during lateral compression.

In Example 5, the commercial product, KOTEX™ Ultrathin Maxi with Wings was used. This product features a "SAFETY ZONE™" design, comprising a nonwoven transfer layer underneath a smaller central airlaid strip and superposed over a larger airlaid absorbent member, substantially similar to Example 1. The commercial product, first introduced in 1998, primarily differs from Example 1 in that the commercial product has an apertured film cover and wings. Example 5 was produced by cutting a slit in the topsheet along a longitudinal side of the article to provide access to the upper layer of the article. The upper layer (a central absorbent member) of the article already contained a longitudinal slit, but was further provided with oblique cuts resulting in an appearance substantially similar to that of article 150 in FIG. 12. During lateral compression, the upward deformation of the crotch region was improved in height and definition, being relatively more decoupled from the deformation elsewhere in the article.

In Example 6, an attachment point was added to the article of Example 5 by scraping a small hole (about 0.5 cm in diameter) in the polymeric web between the two absorbent layers and in the lower absorbent at a region on the longitudinal centerline just outside the elevated region within the shaping lines, and then using piece of rolled adhesive tape (thus making it two-sided) to connect the central absorbent member (the upper layer) to the backsheet. Upon laterally compressing the article, the end of the article closest to the attachment region tended to curl upwards along the longitudinal axis. Without the tape, there was some upward deflection of the region that would become the attachment point. When upward deflection of the upper layer was prevented by the presence of the attachment point, the resulting mechanical strains apparently causes the nearby end of the article to deflect upwards instead, a desirable result for improved body fit. Further, the attachment point increased the vertical separation of the upward deflecting crotch region from the taped-down portion of the central absorbent member, resulting in a larger vertical gap about the outwardly spanning lines. The gap could be useful in receiving body fluids during gushes or high flow rate insults, or could provide a place for additional components to be placed, such as odor controlling agents.

It will be appreciated that the foregoing examples, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

We claim:

1. An absorbent article having a crotch region and a body side, the absorbent article comprising:
    a) a liquid impervious backsheet;
    b) a liquid pervious topsheet attached to the backsheet;
    c) an absorbent core positioned between the topsheet and the backsheet, the absorbent core comprising:
        a central absorbent member having a width in the crotch region and including a shaping line, and
        an outer absorbent member having a width in the crotch region greater than the width of the central absorbent member in the crotch region,
        the absorbent core further comprising at least two crease lines in the outer absorbent member or along the boundary between the central absorbent member and the outer absorbent member,
        wherein the at least two crease lines and the shaping line each define a sudden change in material properties of the absorbent core wherein, during lateral compression in the crotch region, the outer absorbent member is adapted to deflect in a direction away from the body side along at least one of the crease lines and the central absorbent member is adapted to deflect in a direction toward the body side along the shaping line.

2. The absorbent article of claim 1, wherein the central absorbent member further comprises first and second longitudinal sides, and wherein at least one crease line is located substantially along a portion of the first longitudinal side of the central absorbent member such that, during lateral compression in the crotch region, a valley having first and second sides is formed along a portion of the first longitudinal side of the central absorbent member, wherein the first side of the valley comprises a portion of the outer absorbent member and the second side of the valley comprises a portion of the central absorbent member.

3. The absorbent article of claim 1, wherein a void space in the absorbent core is created by lateral compression in the crotch region.

4. The absorbent article of claim 1, wherein a gap is created between the central absorbent member and the outer absorbent member during lateral compression.

5. The absorbent article of claim 1, wherein at least one of the crease lines is formed by a method selected from the group consisting of embossing, cuffing, stamping, perforating, notching, tearing, hot pressing, and ultrasonic bonding.

6. The absorbent article of claim 1 wherein the shaping line comprises at least one of the group consisting of a densified area of the central absorbent member, an elongated weakened zone of the central absorbent member, a slit, a cut, a notch, a tear, and perforations.

7. The absorbent article of claim 1 wherein the shaping line comprises bonded regions formed by a method selected from the group consisting of thermobonding, hot pressing, embossing, and ultrasonic bonding.

8. The absorbent article of claim 1 wherein the absorbent article exhibits an increase in Vertical Deformation in the crotch region of at least about 20% relative to the Vertical Deformation in the crotch region exhibited by an essentially identical absorbent article without a shaping line.

9. The absorbent article of claim 1 wherein the absorbent article exhibits a Vertical Deformation in the crotch region of at least about 0.5 centimeter.

10. The absorbent article of claim 1 wherein the absorbent article exhibits an increase in Central Elevation in the crotch region of at least about 20% relative to the Central Elevation in the crotch region exhibited by an essentially identical absorbent article without a shaping line.

11. The absorbent article of claim 1 wherein the absorbent article exhibits a Central Elevation of at least about 1 centimeter.

12. The absorbent article of claim 1 wherein the absorbent article exhibits a decrease in Compressed Radius of Curvature of at least about 20% relative to the Compressed Radius of Curvature exhibited by an essentially identical absorbent article without a shaping line.

13. The absorbent article of claim 1 wherein the absorbent article exhibits a Compressed Radius of Curvature no greater than about 0.5 centimeter.

14. The absorbent article of claim 1 further comprising a transverse centerline, wherein the central absorbent member further comprises longitudinal sides and the shaping line comprises a longitudinal central line comprising two endpoints and, near both of the endpoints, a pair of outward spanning lines having inner and outer endpoints, wherein each inner endpoint is both relatively nearer the longitudinal centerline and relatively nearer the transverse centerline than the corresponding outer endpoint.

15. The absorbent article of claim 1 wherein the central absorbent member further comprises longitudinal sides and a longitudinal centerline and the shaping line comprises a longitudinal component near the longitudinal centerline of the article and oblique components traversing a distance from the vicinity of the longitudinal centerline to the longitudinal sides of the central absorbent member.

16. The absorbent article of claim 1, wherein the central absorbent member is disposed above a portion of the outer absorbent member.

17. The absorbent article of claim 1, wherein the outer absorbent member comprises a central void space for receiving the central absorbent member.

18. The absorbent article of claim 1, further comprising at least one attachment point attaching the central absorbent member to the backsheet.

19. An absorbent article, the article having a crotch region, a body side, and a garment side, the absorbent article comprising:
   a) a liquid impervious backsheet;
   b) a liquid pervious topsheet attached to the backsheet;
   c) an absorbent core positioned between the topsheet and the backsheet, the absorbent core comprising an upper layer toward the body side and a lower layer toward the garment side, the upper layer comprising a shaping line and the absorbent core further comprising crease lines substantially not within the upper layer; and
   d) a polymeric web disposed between the upper layer and lower layer of the absorbent article.

20. The absorbent article of claim 19, wherein the lower layer comprises a central depression for receiving at least a portion of the upper layer.

21. The absorbent article of claim 19, wherein the lower layer is wider than the upper layer and the absorbent article further comprises a longitudinal boundary between the upper layer and the lower layer that serves as a crease line.

22. The absorbent article of claim 19, wherein the shaping line comprises at least one of the group consisting of a densified area of the upper layer, an elongated weakened zone of the upper layer, a slit, a cut, a notch, a tear, and perforations.

23. The absorbent article of claim 19, wherein the absorbent article exhibits an increase in Vertical Deformation in the crotch region of at least about 20% relative to the Vertical Deformation in the crotch region exhibited by an essentially identical absorbent article without a shaping line.

24. The absorbent article of claim 19, wherein the absorbent article exhibits a Vertical Deformation of at least about 0.5 centimeter.

25. The absorbent article of claim 19, wherein the absorbent article exhibits an increase in Central Elevation in the crotch region of at least about 20% relative to the Central Elevation in the crotch region exhibited by an essentially identical absorbent article without a shaping line.

26. The absorbent article of claim 19, wherein the absorbent article exhibits a Central Elevation of at least about 1 centimeter.

27. The absorbent article of claim 19, wherein the polymeric web is impervious to liquid.

28. The absorbent article of claim 19, wherein the polymeric web is a fibrous nonwoven web.

29. The absorbent article of claim 1, further comprising a wicking barrier between the central absorbent member and the outer absorbent member.

30. The absorbent article of claim 29, wherein the wicking baffler is impervious.

31. The absorbent article of claim 29, wherein the wicking barrier is porous.

32. The absorbent article of claim 29, wherein the wicking barrier comprises a film.

33. The absorbent article of claim 19, wherein the polymeric web comprises a polyolefin film.

34. The absorbent article of claim 19, wherein the polymeric web comprises a foam layer.

35. The absorbent article of claim 19, wherein the polymeric web has a thickness of about 0.2 mm or less.

36. The absorbent article of claim 19, wherein the polymeric web comprises a fibrous web impregnated with hydrophobic matter.

* * * * *